(12) United States Patent
LaVon

(10) Patent No.: US 8,187,239 B2
(45) Date of Patent: May 29, 2012

(54) SIDE NOTCHED FOLDED DIAPER

(75) Inventor: Gary Dean LaVon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 326 days.

(21) Appl. No.: 11/140,888

(22) Filed: May 31, 2005

(65) Prior Publication Data

US 2006/0271005 A1    Nov. 30, 2006

(51) Int. Cl.
*A61F 13/15* (2006.01)
*A61F 13/20* (2006.01)

(52) U.S. Cl. ............... 604/385.01; 604/385.04; 604/378

(58) Field of Classification Search ............ 604/385.01, 604/385.21, 35.24–385.3
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |
| 1,989,283 A | 6/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,207,158 A | 9/1965 | Yoshitake et al. |
| 3,386,442 A | 6/1968 | Sabee |

(Continued)

FOREIGN PATENT DOCUMENTS

EP   0 206 208   12/1986

(Continued)

OTHER PUBLICATIONS

U.S. Appl. No. 11/133,818, filed May 20, 2005, LaVon et al.

(Continued)

*Primary Examiner* — Michele Kidwell
(74) *Attorney, Agent, or Firm* — Richard L. Alexander

(57) ABSTRACT

A disposable absorbent article includes a chassis and an absorbent assembly. The chassis includes a water-impermeable backsheet that is folded laterally inward at both of its side edges to form laterally opposing side flaps. Each side flap is attached to the interior surface of the chassis adjacent to its end edges. Each side flap has a longitudinally extending elastic gathering member attached adjacent to its proximal edge. Each side flap is also attached to the interior surface of the chassis at continuous longitudinally extending laterally opposing water-impermeable side seals. The chassis is side notched to give it an hourglass shape. The chassis may include an extensible formed web material. The absorbent assembly includes an absorbent core that may contain superabsorbent particles, which may be contained inside pockets. The absorbent assembly may be attached in a cruciform pattern to the chassis to allow portions of the chassis to extend laterally.

18 Claims, 17 Drawing Sheets

U.S. PATENT DOCUMENTS

| | | | |
|---|---|---|---|
| 3,561,446 A | 2/1971 | Jones | |
| 3,572,342 A | 3/1971 | Lindquist et al. | |
| 3,572,432 A | 3/1971 | Aulick | |
| 3,578,155 A | 5/1971 | Small et al. | |
| 3,610,244 A | 10/1971 | Jones | |
| 3,618,608 A | 11/1971 | Brink | |
| 3,642,001 A | 2/1972 | Sabee | |
| 3,653,381 A | 4/1972 | Warnken | |
| 3,688,767 A | 9/1972 | Goldstein | |
| 3,710,797 A | 1/1973 | Marsan | |
| 3,731,688 A | 5/1973 | Litt et al. | |
| 3,756,878 A | 9/1973 | Willot | |
| 3,774,241 A | 11/1973 | Zerkle | |
| 3,776,233 A | 12/1973 | Schaar | |
| 3,814,100 A | 6/1974 | Nystrand et al. | |
| 3,840,418 A | 10/1974 | Sabee | |
| 3,847,702 A | 11/1974 | Jones | |
| 3,848,595 A | 11/1974 | Endres | |
| 3,848,597 A | 11/1974 | Endres | |
| 3,860,003 A | 1/1975 | Buell | |
| 3,863,637 A | 2/1975 | MacDonald et al. | |
| 3,882,870 A | 5/1975 | Hathaway | |
| 3,884,234 A | 5/1975 | Taylor | |
| 3,900,032 A | 8/1975 | Heurlen | |
| 3,920,017 A | 11/1975 | Karami | |
| 3,924,626 A | 12/1975 | Lee et al. | |
| 3,926,189 A | 12/1975 | Taylor | |
| 3,929,134 A | 12/1975 | Karami | |
| 3,929,135 A | 12/1975 | Thompson | |
| 3,930,501 A | 1/1976 | Schaar | |
| 3,938,523 A | 2/1976 | Gilliland et al. | |
| 3,968,799 A | 7/1976 | Schrading | |
| 3,978,861 A | 9/1976 | Schaar | |
| 3,981,306 A | 9/1976 | Krusko | |
| 3,987,794 A | 10/1976 | Schaar | |
| 3,995,637 A | 12/1976 | Schaar | |
| 3,995,640 A | 12/1976 | Schaar | |
| 3,999,547 A | 12/1976 | Hernandez | |
| 4,014,338 A | 3/1977 | Schaar | |
| 4,034,760 A | 7/1977 | Amirsakis | |
| 4,074,508 A | 2/1978 | Reid | |
| 4,084,592 A | 4/1978 | Tritsch | |
| 4,100,922 A | 7/1978 | Hernandez | |
| 4,257,418 A | 3/1981 | Hessner | |
| 4,296,750 A | 10/1981 | Woon et al. | |
| 4,315,508 A | 2/1982 | Bolick | |
| 4,324,246 A | 4/1982 | Mullane et al. | |
| 4,342,314 A | 8/1982 | Radel et al. | |
| 4,388,075 A | 6/1983 | Mesek et al. | |
| 4,461,621 A | 7/1984 | Karami et al. | |
| 4,463,045 A | 7/1984 | Ahr et al. | |
| 4,475,912 A | 10/1984 | Coates | |
| 4,490,148 A | 12/1984 | Beckeström | |
| 4,585,450 A | 4/1986 | Rosch et al. | |
| 4,589,878 A | 5/1986 | Mitrani | |
| 4,601,717 A | 7/1986 | Blevins | |
| 4,610,678 A | 9/1986 | Weisman et al. | |
| 4,636,207 A | 1/1987 | Buell | |
| 4,670,011 A | 6/1987 | Mesek | |
| 4,680,030 A | 7/1987 | Coates et al. | |
| 4,681,581 A | 7/1987 | Coates | |
| 4,690,680 A | 9/1987 | Higgins | |
| 4,695,278 A | 9/1987 | Lawson | |
| 4,704,115 A | 11/1987 | Buell | |
| 4,704,116 A | 11/1987 | Enloe | |
| 4,731,066 A | 3/1988 | Korpman | |
| 4,747,846 A | 5/1988 | Boland et al. | |
| 4,795,454 A | 1/1989 | Dragoo | |
| 4,802,884 A | 2/1989 | Fröidh et al. | |
| 4,808,176 A | 2/1989 | Kielpikowski | |
| 4,834,735 A | 5/1989 | Alemany et al. | |
| 4,834,740 A | 5/1989 | Suzuki et al. | |
| 4,834,742 A | 5/1989 | Wilson et al. | |
| 4,838,886 A | 6/1989 | Kent | |
| 4,846,825 A | 7/1989 | Enloe et al. | |
| 4,861,652 A | 8/1989 | Lippert et al. | |
| 4,888,231 A | 12/1989 | Angstadt | |
| 4,892,528 A | 1/1990 | Suzuki et al. | |
| 4,892,536 A | 1/1990 | DesMarais et al. | |
| 4,904,251 A | 2/1990 | Igaue et al. | |
| 4,909,802 A | 3/1990 | Ahr et al. | |
| 4,909,803 A | 3/1990 | Aziz et al. | |
| 4,940,463 A | 7/1990 | Leathers et al. | |
| 4,940,464 A | 7/1990 | Van Gompel et al. | |
| 4,950,264 A | 8/1990 | Osborn | |
| 4,963,140 A | 10/1990 | Robertson et al. | |
| 4,968,313 A | 11/1990 | Sabee | |
| 4,990,147 A | 2/1991 | Freeland | |
| 5,006,394 A | 4/1991 | Baird | |
| 5,032,120 A | 7/1991 | Freeland et al. | |
| 5,037,416 A | 8/1991 | Allen et al. | |
| 5,071,414 A | 12/1991 | Elliott | |
| 5,085,654 A | 2/1992 | Buell | |
| 5,092,861 A | 3/1992 | Nomura et al. | |
| 5,114,420 A | 5/1992 | Igaue et al. | |
| 5,135,522 A | 8/1992 | Fahrenkrug et al. | |
| D329,697 S | 9/1992 | Fahrenkrug et al. | |
| 5,151,092 A | 9/1992 | Buell et al. | |
| 5,190,606 A | 3/1993 | Merkatoris et al. | |
| 5,204,997 A | 4/1993 | Suzuki et al. | |
| 5,221,274 A | 6/1993 | Buell et al. | |
| 5,235,515 A | 8/1993 | Ungpiyakul et al. | |
| 5,246,431 A | 9/1993 | Minetola et al. | |
| 5,246,432 A | 9/1993 | Suzuki et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,312,386 A | 5/1994 | Correa et al. | |
| 5,358,500 A | 10/1994 | LaVon et al. | |
| 5,366,782 A | 11/1994 | Curro et al. | |
| 5,387,209 A | 2/1995 | Yamamoto et al. | |
| 5,397,316 A | 3/1995 | LaVon et al. | |
| H1440 H | 5/1995 | New et al. | |
| H1440 H | 5/1995 | New et al. | |
| 5,476,458 A | 12/1995 | Glaug et al. | |
| 5,518,801 A | 5/1996 | Chappell et al. | |
| 5,531,730 A | 7/1996 | Dreier | |
| 5,549,592 A | 8/1996 | Fries et al. | |
| 5,549,593 A | 8/1996 | Ygge et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,584,829 A | 12/1996 | Lavash et al. | |
| 5,607,416 A | 3/1997 | Yamamoto et al. | |
| 5,607,537 A | 3/1997 | Johnson et al. | |
| 5,607,760 A | 3/1997 | Roe | |
| 5,609,587 A | 3/1997 | Roe | |
| 2,788,786 A | 4/1997 | Dexter | |
| 5,622,589 A | 4/1997 | Johnson et al. | |
| 5,624,424 A | 4/1997 | Saisaka et al. | |
| 5,625,222 A | 4/1997 | Yoneda et al. | |
| 5,626,571 A | 5/1997 | Young et al. | |
| 5,635,191 A | 6/1997 | Roe et al. | |
| 5,643,243 A | 7/1997 | Klemp | |
| 5,643,588 A | 7/1997 | Roe et al. | |
| H1674 H | 8/1997 | Ames et al. | |
| 5,662,638 A | 9/1997 | Johnson et al. | |
| 5,674,215 A | 10/1997 | Ronnberg | |
| 5,691,035 A | 11/1997 | Chappell et al. | |
| 5,723,087 A | 3/1998 | Chappell et al. | |
| 5,749,866 A | 5/1998 | Roe et al. | |
| 5,752,947 A | 5/1998 | Awolin | |
| 5,772,825 A | 6/1998 | Schmitz | |
| 5,776,121 A * | 7/1998 | Roe et al. | 604/385.25 |
| 5,779,831 A | 7/1998 | Schmitz | |
| 5,797,894 A | 8/1998 | Cadieux et al. | |
| 5,810,800 A | 9/1998 | Hunter et al. | |
| 5,814,035 A | 9/1998 | Gryskiewicz et al. | |
| 5,846,232 A | 12/1998 | Serbiak et al. | |
| 5,851,204 A | 12/1998 | Mizutani | |
| 5,865,823 A | 2/1999 | Curro | |
| 5,873,868 A | 2/1999 | Nakahata | |
| 5,876,391 A | 3/1999 | Roe et al. | |
| 5,891,544 A | 4/1999 | Chappell et al. | |
| 5,897,545 A | 4/1999 | Kline et al. | |
| 5,904,673 A | 5/1999 | Roe et al. | |

| | | |
|---|---|---|
| 5,931,825 A | 8/1999 | Kuen et al. |
| 5,951,536 A | 9/1999 | Osborn, III et al. |
| 5,957,908 A | 9/1999 | Kline et al. |
| 5,968,029 A | 10/1999 | Chappell et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,102,892 A | 8/2000 | Putzer et al. |
| 6,107,537 A | 8/2000 | Elder et al. |
| 6,110,157 A | 8/2000 | Schmidt |
| 6,117,121 A | 9/2000 | Faulks et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,129,720 A | 10/2000 | Blenke et al. |
| 6,156,424 A | 12/2000 | Taylor |
| 6,165,160 A | 12/2000 | Suzuki et al. |
| 6,174,302 B1 | 1/2001 | Kumasaka |
| 6,177,607 B1 | 1/2001 | Blaney et al. |
| 6,186,996 B1 | 2/2001 | Martin |
| 6,210,390 B1 | 4/2001 | Karlsson |
| 6,238,380 B1 | 5/2001 | Sasaki |
| 6,241,716 B1 | 6/2001 | Rönnberg |
| 6,322,552 B1 | 11/2001 | Blenke et al. |
| 6,325,787 B1 | 12/2001 | Roe et al. |
| 6,334,858 B1 | 1/2002 | Rönnberg et al. |
| 6,350,332 B1 | 2/2002 | Thomas et al. |
| 6,402,729 B1 | 6/2002 | Boberg et al. |
| 6,402,731 B1 | 6/2002 | Suprise et al. |
| 6,410,820 B1 | 6/2002 | McFall et al. |
| 6,413,249 B1 | 7/2002 | Turi et al. |
| 6,419,667 B1 | 7/2002 | Avalon et al. |
| 6,432,098 B1 | 8/2002 | Kline et al. |
| 6,432,099 B2 | 8/2002 | Rönnberg |
| 6,443,933 B1 | 9/2002 | Suzuki et al. |
| 6,461,342 B2 | 10/2002 | Tanji et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,520,947 B1 | 2/2003 | Tilly et al. |
| 6,524,294 B1 | 2/2003 | Hilston et al. |
| 6,585,713 B1 | 7/2003 | LeMahieu et al. |
| 6,602,234 B2 | 8/2003 | Klemp et al. |
| 6,605,070 B2 | 8/2003 | Ludwig et al. |
| 6,648,869 B1 | 11/2003 | Schlinz et al. |
| 6,648,870 B2 | 11/2003 | Itoh et al. |
| 6,648,871 B2 | 11/2003 | Kusibojoska et al. |
| 6,682,515 B1 | 1/2004 | Mizutani et al. |
| 6,689,115 B1 | 2/2004 | Popp et al. |
| 6,726,792 B1 | 4/2004 | Johnson et al. |
| 6,818,083 B2 | 11/2004 | Mcamish et al. |
| 6,880,211 B2 | 4/2005 | Jackson et al. |
| 6,923,797 B2 | 8/2005 | Shinohara et al. |
| 6,962,578 B1 | 11/2005 | LaVon |
| 6,972,010 B2 | 12/2005 | Pesce et al. |
| 7,014,632 B2 | 3/2006 | Takino et al. |
| 7,037,299 B2 | 5/2006 | Turi et al. |
| 7,048,726 B2 | 5/2006 | Kusagawa et al. |
| 7,160,281 B2 | 1/2007 | Leminh et al. |
| 2002/0045881 A1 | 4/2002 | Kusibojoska et al. |
| 2002/0087139 A1 | 7/2002 | Popp et al. |
| 2002/0144644 A1 | 10/2002 | Zehnder et al. |
| 2002/0151861 A1 | 10/2002 | Klemp et al. |
| 2002/0173767 A1 | 11/2002 | Popp et al. |
| 2003/0088223 A1 | 5/2003 | Vogt et al. |
| 2003/0144644 A1 | 7/2003 | Murai et al. |
| 2003/0148694 A1 | 8/2003 | Ghiam |
| 2003/0233082 A1 | 12/2003 | Kline et al. |
| 2004/0022998 A1 | 2/2004 | Miyamoto et al. |
| 2004/0082928 A1 | 4/2004 | Pesce et al. |
| 2004/0122411 A1 | 6/2004 | Hancock-Cooke |
| 2004/0127890 A1 | 7/2004 | Bacher |
| 2004/0147890 A1 | 7/2004 | Nakahata et al. |
| 2004/0162536 A1 | 8/2004 | Becker et al. |
| 2004/0167486 A1 | 8/2004 | Busam et al. |
| 2004/0225271 A1 | 11/2004 | Datta et al. |
| 2004/0236299 A1 | 11/2004 | Tsang et al. |
| 2004/0249355 A1 | 12/2004 | Tanio et al. |
| 2005/0004548 A1 | 1/2005 | Otsubo et al. |
| 2005/0038401 A1 | 2/2005 | Suzuki et al. |
| 2005/0085784 A1 | 4/2005 | LeMinh et al. |
| 2005/0171499 A1 | 8/2005 | Nigam et al. |
| 2005/0203475 A1 | 9/2005 | LaVon et al. |
| 2005/0288645 A1 | 12/2005 | LaVon et al. |
| 2005/0288646 A1 | 12/2005 | LaVon |
| 2006/0264860 A1 | 11/2006 | Beck |

FOREIGN PATENT DOCUMENTS

| | | |
|---|---|---|
| EP | 0 206 208 A1 | 12/1986 |
| EP | 0 403 832 B1 | 12/1990 |
| EP | 0 761 194 A2 | 3/1997 |
| EP | 0 893 115 A2 | 1/1999 |
| EP | 0 916 327 B1 | 5/1999 |
| EP | 0 951 890 A2 | 10/1999 |
| EP | 0 793 469 B9 | 6/2002 |
| EP | 1 224 922 A2 | 7/2002 |
| EP | 1 447 066 A1 | 8/2004 |
| EP | 1 447 067 A1 | 8/2004 |
| ES | 2 213 491 A1 | 8/2004 |
| FR | 2 566 631 A1 | 1/1986 |
| FR | 2 612 770 A1 | 9/1988 |
| FR | 2 810 234 | 12/2001 |
| FR | 2 810 234 A1 | 12/2001 |
| GB | 1 307 441 | 2/1973 |
| GB | 1 513 055 | 6/1978 |
| GB | 1 513 055 | 5/1982 |
| GB | 2 101 468 | 1/1983 |
| GB | 2 101 468 A | 1/1983 |
| GB | 2 262 873 A | 7/1993 |
| JP | 04 122256 | 4/1992 |
| JP | 04 122256 A | 4/1992 |
| JP | 11318980 | 11/1999 |
| WO | WO 95/29657 | 11/1995 |
| WO | WO 95/29657 A1 | 11/1995 |
| WO | WO 98/16179 A1 | 4/1998 |
| WO | WO 99/13813 A1 | 3/1999 |
| WO | WO 03/009794 A3 | 2/2003 |
| WO | WO 2004/105664 | 12/2004 |
| WO | WO 2005/087164 A1 | 9/2005 |
| WO | WO 2007/000315 | 1/2007 |
| WO | WO 2007/000315 A1 | 1/2007 |

OTHER PUBLICATIONS

U.S. Appl. No. 11/135,689, filed May 24, 2005, LaVon.
U.S. Appl. No. 11/197,197, filed Aug. 4, 2005, LaVon et al.
U.S. Appl. No. 11/210,345, filed Aug. 24, 2005, LaVon et al.
U.S. Appl. No. 11/286,934, filed Nov. 23, 2005, LaVon et al.
International Search Report—PCT/US2006/016557—Jul. 25, 2006.

* cited by examiner

SIDE NOTCHED FOLDED DIAPER

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact. As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

A disposable absorbent article includes a chassis and an absorbent assembly. The chassis includes a water-impermeable backsheet that is folded laterally inward at both of its side edges to form laterally opposing side flaps. Each side flap is attached to the interior surface of the chassis adjacent to its end edges. Each side flap has a longitudinally extending elastic gathering member attached adjacent to its proximal edge. Each side flap is also attached to the interior surface of the chassis at continuous longitudinally extending laterally opposing water-impermeable side seals. The chassis is side notched to give it an hourglass shape. The chassis may include an extensible formed web material. The absorbent assembly includes an absorbent core that may contain superabsorbent particles, which may be contained inside pockets. The absorbent assembly may be attached in a cruciform pattern to the chassis to allow portions of the chassis to extend laterally.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In FIG. 1, the interior of the diaper 20 is shown facing the viewer.

In FIG. 10, the interior of the diaper 20 is shown facing the viewer.

In FIG. 16, the interior of the diaper 20 is shown facing upward.

DETAILED DESCRIPTION OF THE INVENTION

Figure 1:
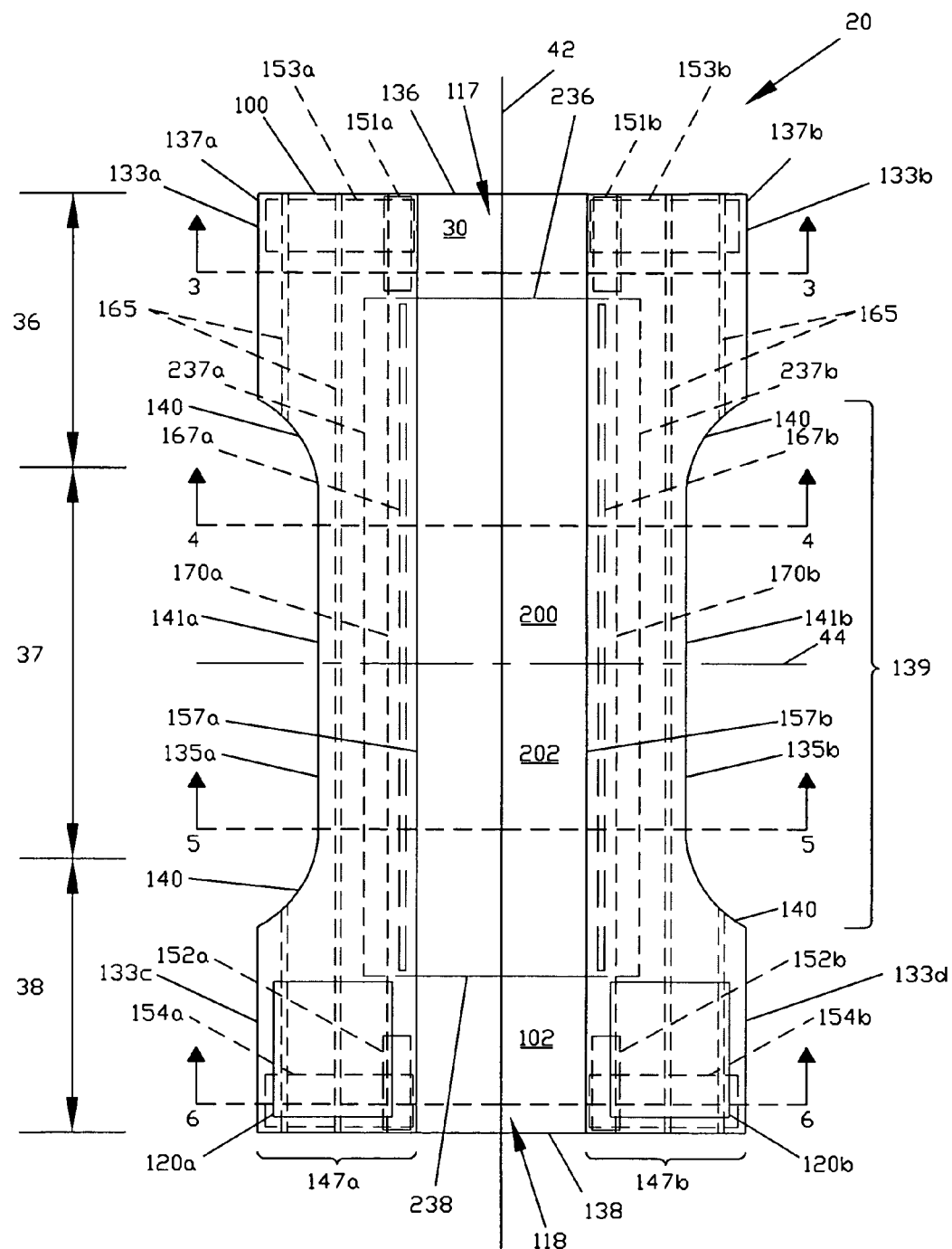
FIG. 1 is a plan view of an exemplary disposable absorbent article in the form of a diaper 20 shown in its flat, uncontracted state, i.e., without the contraction induced by elastic members.

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "longitudinal" refers to a direction running from a waist edge to an opposing waist edge of the article and generally parallel to the maximum linear dimension of the article. Directions within 45° of the longitudinal direction are considered to be "longitudinal".

The term "lateral" refers to a direction running from a side edge to an opposing side edge of the article and generally at a right angle to the longitudinal direction. Directions within 45 degrees of the lateral direction are considered to be "lateral".

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables and Nonwovens Association).

The terms "proximal" and "distal" refer respectively to the location of an element relatively near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

In the following description and in the drawing figures, various structural elements are identified by reference numerals without suffixed letters when referring to the group as a whole and by the same reference numerals with suffixed letters when distinguishing between, for example, left and right members of the group. As an example, the side flaps as a group are identified by the reference numeral 147 while the individual left and right side flaps are respectively designated as elements 147a and 147b.

Description of Exemplary Diaper Embodiment

Reference is made to FIG. 1, FIG. 2, FIG. 3, FIG. 4, FIG. 5, FIG. 6, FIG. 7, FIG. 8, and FIG. 9 for this section of this description.

One end portion of the exemplary diaper 20 is configured as a front waist region 36. The longitudinally opposing end portion is configured as a back waist region 38. An intermediate portion of the diaper 20 extending longitudinally between the front waist region 36 and the back waist region 38 is configured as a crotch region 37.

The basic structure of the diaper 20 includes a chassis 100. The chassis 100 has a laterally extending front waist edge 136 in the front waist region 36 and a longitudinally opposing and laterally extending back waist edge 138 in the back waist region 38. The finished chassis 100 has longitudinally extending front folded side edge segments 133a and 133b in the front waist regions, longitudinally opposing longitudinally extending back folded side edge segments 133c and 133d in the back waist region, and longitudinally extending cut side edge segments 135 in at least the crotch region, each of the cut side edge segments 135 connecting the respective front and back folded side edge segments 133. In combination, the respective folded side edge segments 133 and cut side edge segments 135 form the composite side edges 137, which connect the front waist edge and the back waist edge. The chassis 100 has an interior surface 102 and an exterior surface 104. The chassis 100 also has a longitudinal axis 42 and a lateral axis 44. The longitudinal axis 42 extends through the midpoint of the front waist edge 136 and through the midpoint of the back waist edge 138. The lateral axis 44 extends through the midpoint of the left side edge 137a and through the midpoint of the right side edge 137b. The exemplary chassis 100 shown in FIG. 1 additionally has longitudinally extending and laterally opposing side flaps 147a and 147b that are described in more detail below.

The basic structure of the diaper 20 also includes an absorbent assembly 200 that is attached to the chassis 100. The absorbent assembly 200 has a laterally extending front edge 236 in the front waist region 36 and a longitudinally opposing and laterally extending back edge 238 in the back waist region 38. The absorbent assembly 200 has a longitudinally extending left side edge 237a and a laterally opposing and longitudinally extending right side edge 237b, both absorbent assembly side edges extending longitudinally between the front edge 236 and the back edge 238. The absorbent assembly 200 has an interior surface 202 and an exterior surface 204. The absorbent assembly 200 may be disposed symmetrically with respect to either or both of the longitudinal axis 42 and the lateral axis 44. Alternatively, the absorbent assembly 200 may be disposed asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically with respect to the lateral axis 44. In particular, the absorbent assembly 200 shown in FIG. 1 is disposed asymmetrically toward the front waist region 36.

The respective front and back waist edges and side edges of the absorbent assembly 200 may lie inward of the respective front and back waist edges and side edges of the chassis 100, as in the exemplary diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 may coincide with the corresponding edge or edges of the chassis 100.

When the diaper 20 is worn on the lower torso of a wearer, the front waist edge 136 and the back waist edge 138 encircle the waist of the wearer and the side edges 137 encircle the legs of the wearer. At the same time, the crotch region 37 is generally positioned between the legs of the wearer and the absorbent assembly 200 extends from the front waist region 36 through the crotch region 37 to the back waist region 38.

Description of the Chassis

In FIG. 10, FIG. 11, FIG. 12, FIG. 13, FIG. 14, and FIG. 15, the exemplary chassis 100 is shown laid out flat before portions of the chassis 100 are folded laterally inward, i.e., toward the longitudinal axis 42, to form the side flaps 147 and prior to side notching the chassis to form the hourglass shape as shown in FIG. 1, FIG. 2, FIG. 3, FIG. 4, FIG. 5, and FIG. 6. In this condition of being laid out flat, the chassis 100 has laterally opposing longitudinally extending outer side edges 155. Both of these chassis outer side edges extend longitudinally between the front waist edge 136 and the back waist edge 138. As is described in more detail below, when the side flaps 147 are formed by folding portions of the chassis 100 laterally inward, the outer side edges 155 of the chassis form the respective proximal edges 157 of the side flaps.

The chassis 100 includes a water-impermeable backsheet 26. The backsheet 26 forms an exterior surface that is intended to be placed toward any clothing that is worn over the diaper 20. Many suitable materials for use as the backsheet 26 are well-known, including films of polyethylene and other polyolefins. A multi-layer backsheet, such as a laminate of a film 30 and a nonwoven material 31 or a laminate of multiple nonwoven layers, may also be suitable for use as the backsheet 26. Such a backsheet may be oriented with the nonwoven 31 disposed exteriorly of the film, as shown in FIG. 1, FIG. 2, FIG. 3, FIG. 4, FIG. 5, and FIG. 6, to provide the feel and appearance of a more cloth-like outermost layer than would be provided by using the film 30 as the outermost layer.

The chassis 100 may, but need not, additionally include an inner liner attached to the backsheet 26. The inner liner may form a portion of the interior surface 102 of the chassis 100 that is intended to be placed against the body of the wearer. The inner liner preferably is formed of a soft material that will not irritate the skin of the wearer. Such an inner liner may serve to isolate the skin of the wearer from a portion of the backsheet 26 as may be desirable, for example, when the diaper 20 is worn under conditions in which contact between the skin and a backsheet film could be uncomfortable. Many suitable materials for the inner liner are well-known in the art, including rayon and synthetic nonwovens such as spunbonded or carded polypropylene or polyester.

One or more of the edges of the inner liner may lie inward of the edges of the backsheet 26. For example, with reference to the exemplary diaper 20 shown in FIG. 1, only the portions of the inner liner lying in the gaps between the front edge 236 of the absorbent assembly 200 and the front waist edge 136 of the chassis 100 and between the back edge 238 of the absorbent assembly 200 and the back waist edge 138 of the chassis 100 are exposed, while the remainder of the inner liner is covered by the absorbent assembly 200 and the side flaps 147. Therefore, a laterally extending strip of the inner liner disposed in the gap in the front waist region 36 and a similar laterally extending strip of the inner liner disposed in the gap in the back waist region 38 may suffice to isolate the skin of the wearer from the backsheet 26 in these two gaps.

Figure 17:
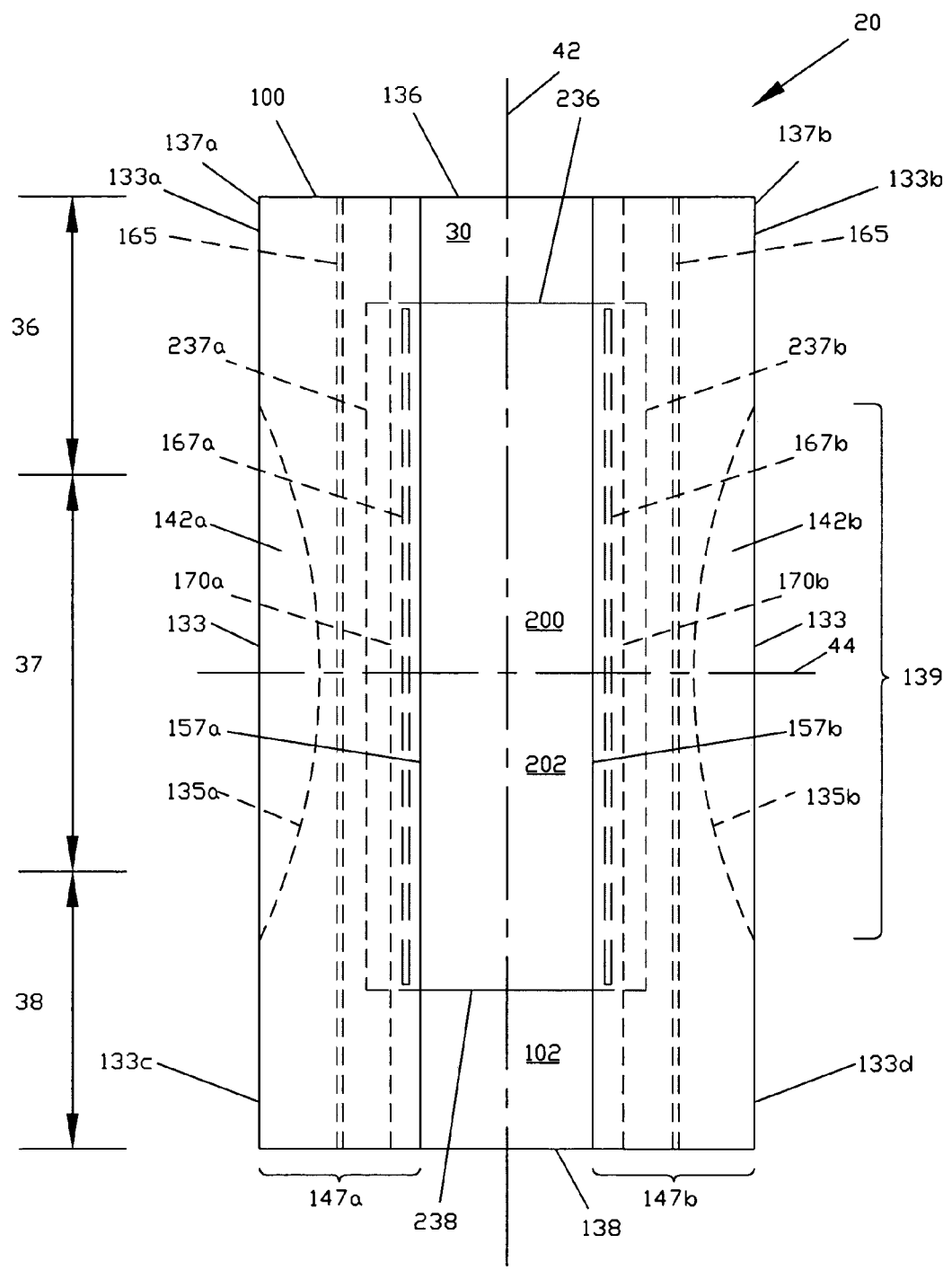
FIG. 17 is a plan view of an exemplary diaper 20 shown in its flat, uncontracted state, after the side flaps 147 are formed by folding portions of the chassis 100 laterally inward, before the side notches 139 are formed by removing side portions 142.

As shown in FIG. 1, FIG. 2, FIG. 3, FIG. 4, FIG. 5, and FIG. 6, the exemplary chassis 100 has longitudinally extending and laterally opposing side flaps 147 that are disposed on the interior portion of the diaper 20 that faces inwardly toward the wearer and contacts the wearer. The side flaps 147 are formed by folding portions of the chassis 100 laterally inward, i.e., toward the longitudinal axis 42. As shown in FIG. 17, this folding of portions of the chassis 100 laterally inward forms both the side flaps 147 and the laterally opposing folded side edges 133. The chassis 100 may simply be folded loosely or may be creased along a portion of each of its folded side edges 133. Alternatively or in addition to creasing, a portion of each of the folded side flaps 147 adjacent to the folded side edges 133 may be attached to the interior surface 102 of the chassis 100 to achieve a similar result.

In the intermediate form of the diaper 20 prior to forming the side notches shown in FIG. 17, the folded side edges 133 extend continuously between the front and back waist edges 136 and 138. Thus, the chassis 100 has a rectangular shape in this intermediate form, albeit narrower than the rectangular shape prior to the folding shown in FIG. 10 and FIG. 11. As will be explained below, the finished diaper 20 is given the hourglass shape shown in FIG. 1 and FIG. 2 by the removal of laterally opposing portions 142 of the chassis in order to form the side notches 139.

For embodiments in which the backsheet comprises a film, portions of the film backsheet 26 that are folded laterally inward to form the side flaps may contact the skin of a wearer during the use of the diaper 20. However, the alternating ridges and valleys in such a film backsheet that has been deformed in order to make it extensible may provide channels through which air can pass to alleviate any concern regarding such contact of the film backsheet with the skin.

The left side flap 147a has a proximal edge 157a and the right side flap 147b has a proximal edge 157b. In the exemplary diaper 20 shown in FIG. 1, the side flaps 147 overlap the absorbent assembly 200, i.e., the proximal edges 157 lie laterally inward of the respective side edges 237 of the absorbent assembly 200. Such an overlapped configuration may be desirable in order to impart a more finished appearance to the diaper 20 than that imparted by a non-overlapped configuration. Alternatively, the side flaps 147 may not overlap the absorbent assembly 200.

In the exemplary chassis 100 shown in FIG. 1, the side flaps 147 extend the full length of the chassis 100 between the front waist edge 136 and the back waist edge 138. Such a full length configuration may be desirable in order to minimize the amount of scrap material and the difficulty associated with the manufacture of the diaper 20, especially when the method used to manufacture the diaper 20 requires the introduction of the material or materials for the chassis 100 in the form of a continuous web or multiple continuous webs. Alternatively, the side flaps may be shorter and extend less than the full distance between the front waist edge 136 and the back waist edge 138. Such a shorter configuration may be desirable in order to minimize the total amount of material used in the manufacture of the diaper 20.

Each of the side flaps 147 is attached to the interior surface 102 of the chassis 100 in attachment zones located in the front waist region 36 and in the back waist region 38 adjacent to the longitudinally distal ends of the side flap. For example, in the exemplary chassis 100 shown in FIG. 1, the side flaps 147 are attached to the interior surface 102 of the chassis 100 in the longitudinally oriented attachment zones 151 and 152. These longitudinally oriented attachment zones may have equal areas or may be unequal in area. For example, the front longitudinally oriented attachment zones 151 may be of one size and the back longitudinally oriented attachment zones 152 may be of another size. In the exemplary chassis 100 shown in FIG. 1, the side flaps 147 are also attached to the interior surface 102 of the chassis 100 in laterally oriented attachment zones 153 adjacent to the front waist edge 136 and in a longitudinally opposing laterally oriented attachment zones 154 adjacent to the back waist edge 138. These laterally oriented attachment zones may similarly have equal areas or may be unequal in area.

Alternatively, each attachment zone may extend laterally across the full width of the respective side flap. For example, a laterally oriented adhesive attachment zone may extend laterally from the chassis left side edge 137a to the left side flap proximal edge 157a and thereby attach the entire width of the left side flap 147a adjacent to the front waist edge 136 to the interior surface 102 of the chassis 100. In embodiments in which the side flaps 147 overlap the absorbent assembly 200, the side flaps 147 may be attached to the absorbent assembly 200 instead of, or in addition to, being attached to the interior surface 102 of the chassis 100.

Between the attachment zones, the proximal edges 157 of the side flaps 147 remain free, i.e., are not attached to the interior surface 102 of the chassis 100 or to the absorbent assembly 200. Also between the attachment zones, each side flap preferably includes a longitudinally extensible flap elastic gathering member that is attached adjacent to the proximal edge of the side flap by any of many well-known means. Each such flap elastic gathering member may be attached over its entire length or over only a portion of its length. For example, such a flap elastic gathering member may be attached only at or near its longitudinally opposing ends and may be unattached at the middle of its length. Such a flap elastic gathering member may be disposed in the crotch region 37 and may extend into one or both of the front waist region 36 and the back waist region 38. For example, in the exemplary chassis 100 shown in FIG. 1, an elastic strand 167 is attached adjacent to the proximal edge 157 of each of the side flaps 147 and extends into both the front waist region 36 and the back waist region 38.

Each flap elastic gathering member may be enclosed inside a folded hem. For example, in the exemplary chassis 100 shown in FIG. 4 and FIG. 5, each of the elastic strands 167 is enclosed inside a hem 170 formed adjacent to the proximal edge 157 of the respective side flap 147. Alternatively, the flap elastic gathering member may be sandwiched between two layers of the chassis, e.g., between the layers of a laminate backsheet or between a backsheet and an inner liner. As another alternative, the flap elastic gathering member may be attached on a surface of the chassis 100 and remain exposed.

Figure 16:
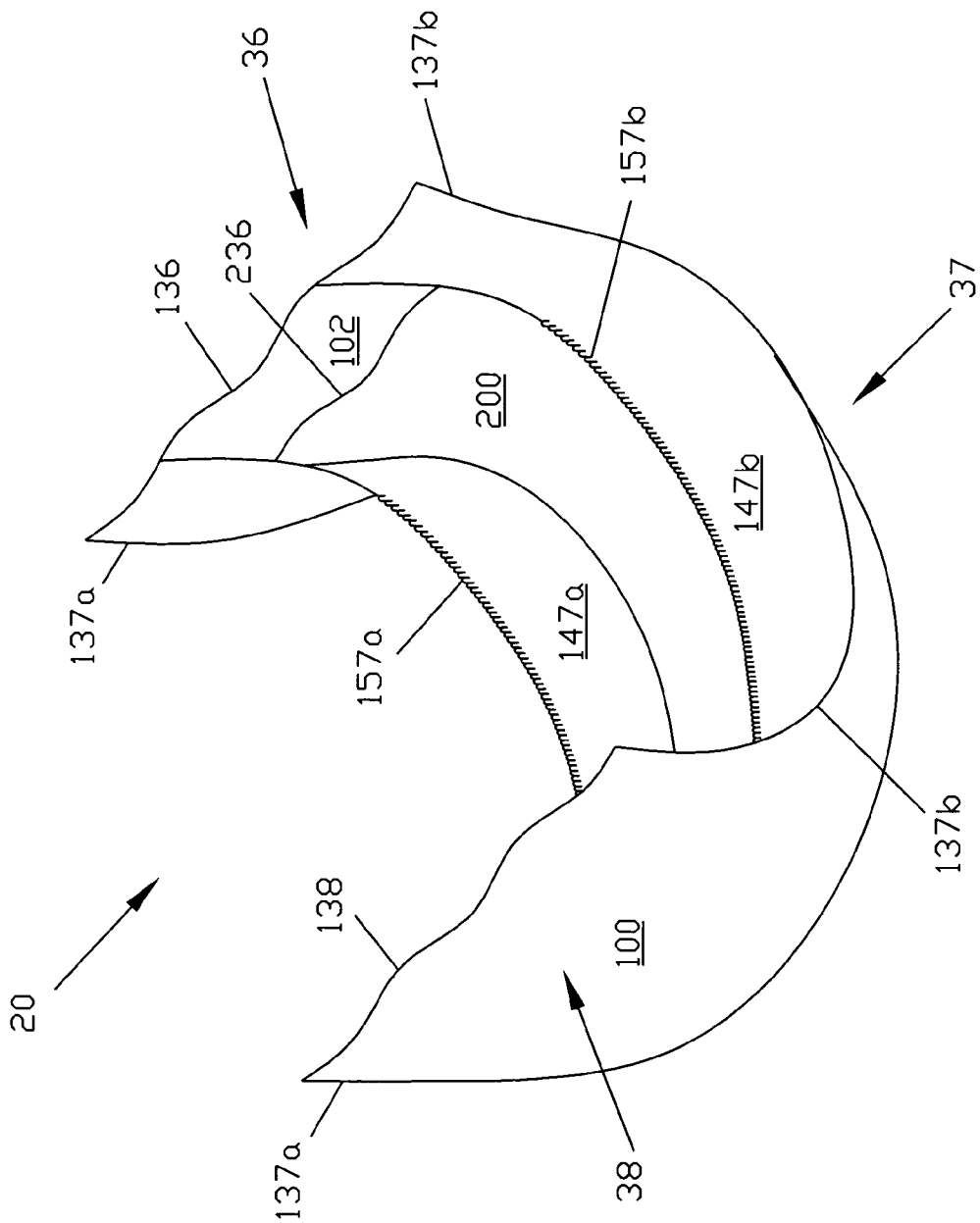
FIG. 16 is a perspective view of an exemplary diaper 20 shown in its relaxed, contracted state, i.e., with the contraction induced by elastic members.

When stretched, the flap elastic gathering member adjacent to each side flap edge allows the side flap edge to extend to the flat uncontracted length of the chassis, e.g., the length of the chassis 100, as shown in FIG. 1. When allowed to relax, the flap elastic gathering member contracts to gather the portion of the side flap edge along which the flap elastic gathering member is attached and thereby make the relaxed length of the side flap edge less than the flat uncontracted length of the chassis. For example, when the exemplary diaper 20 is in a relaxed condition as shown in FIG. 16, the elastic strands 167 contract to gather the proximal edges 157 of the side flaps 147. The contractive forces of the elastic strands 167 are transmitted at the respective front attachment zones 151 and at the respective back attachment zones 152 to the interior surface 102 of the chassis 100. These contractive forces pull the front waist region 36 and the back waist region 38 toward each other and thereby bend the diaper 20 into a "U" shape in which the interior of the "U" shape is formed by the portions of the diaper 20 that are intended to be placed toward the body of the wearer. Because each of the proximal edges 157 remains free between the attachment zones 151 and 152, the contractive force of the elastic strand 167 lifts the proximal edge 157 away from the interior surface 102 of the chassis 100. As shown in FIG. 16, this lifting of the proximal edges 157 when the diaper 20 is in the relaxed condition lifts the side flaps 147 into position to serve as side barriers adjacent to the side edges 237 of the absorbent assembly 200.

When the diaper 20 is worn, the relaxed "U" shape generally conforms to the body of the wearer such that the front waist region 36 and the back waist region 38 are positioned such that they partially encircle the waist and the legs of the wearer. When the diaper 20 is worn in this manner, the elastic strands 167 tend to hold the lifted proximal edges 157 of the side flaps 147 in contact with the body of the wearer and thereby form seals to help prevent the leakage of deposited bodily waste out of the diaper 20. The lateral spacing of the lifted proximal edges 157 is selected to allow the deposit of bodily wastes from the lower torso of the wearer into the space between the lifted side flaps 147 and thereby directly onto the absorbent assembly 200. The width of each of the side flaps 147 in effect becomes its height when the free portion of its proximal edge is lifted and the side flap serves as a side barrier to leakage. This height preferably is selected to allow the lifted proximal edges 157 to fit into the leg creases of the body of the wearer at the same time as the absorbent assembly 200 is held in contact with the body.

Figure 2:
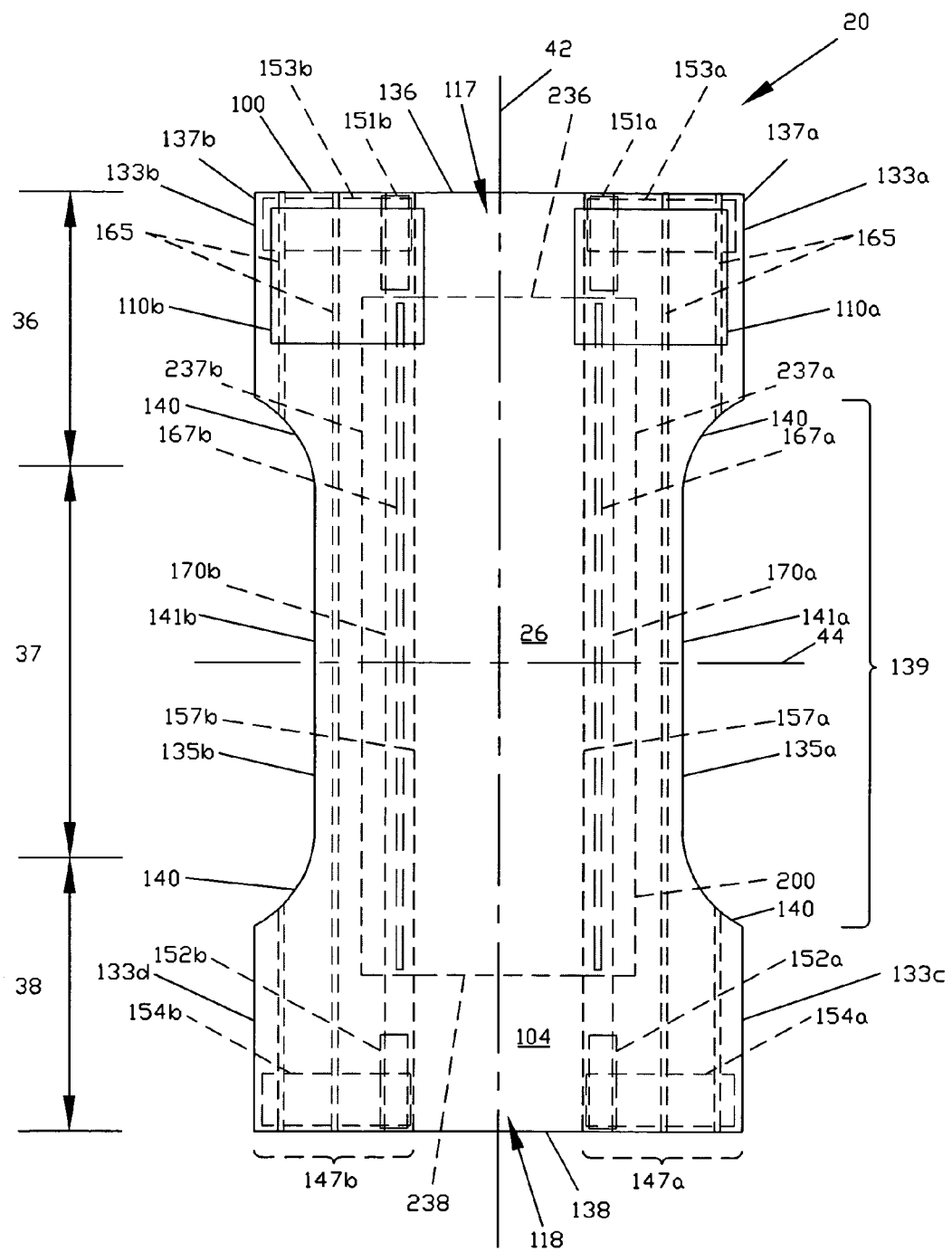
FIG. 2 is a plan view of the diaper 20 of FIG. 1 in its flat, uncontracted state, with the exterior portion of the diaper 20 shown facing the viewer.
Figure 3:
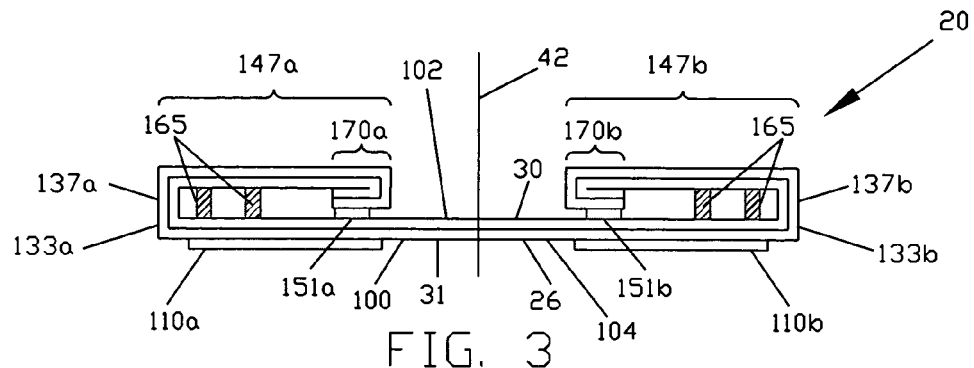
FIG. 3 is a section view of the diaper 20 of FIG. 1 taken at the section line 3-3.
Figure 4:
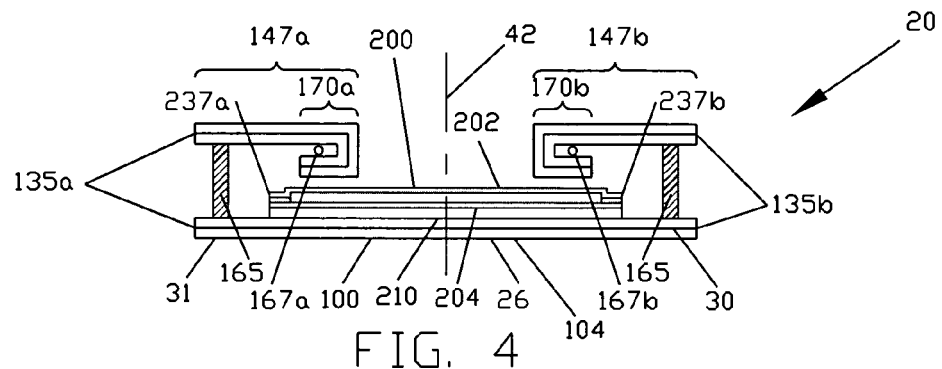
FIG. 4 is a section view of the diaper 20 of FIG. 1 taken at the section line 4-4.
Figure 5:
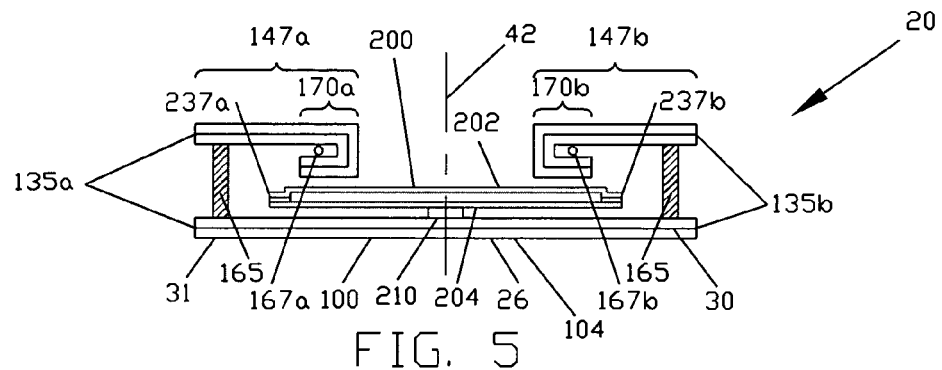
FIG. 5 is a section view of the diaper 20 of FIG. 1 taken at the section line 5-5.
Figure 6:
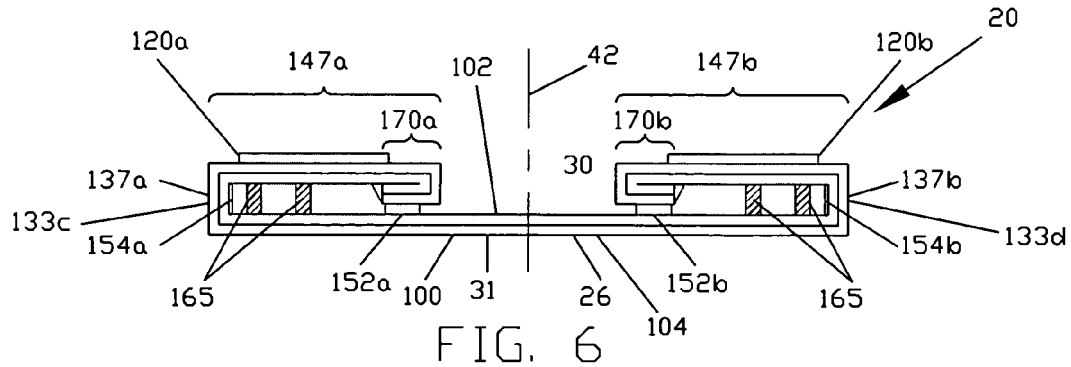
FIG. 6 is a section view of the diaper 20 of FIG. 1 taken at the section line 6-6.
Figure 7:
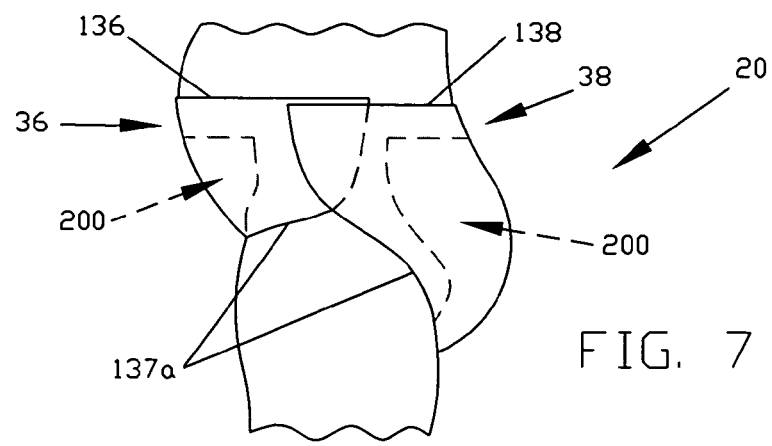
FIG. 7 is a simplified side elevation view of an exemplary diaper 20 being worn about a lower torso of a wearer.
Figure 8:
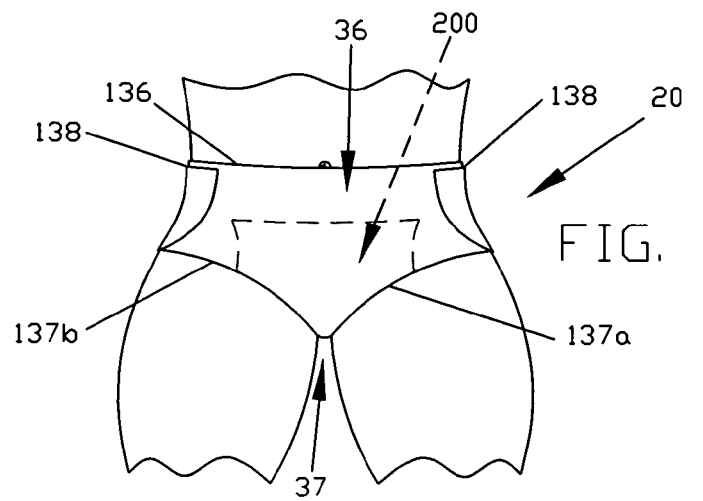
FIG. 8 is a front elevation view of the diaper 20 of FIG. 7.
Figure 9:
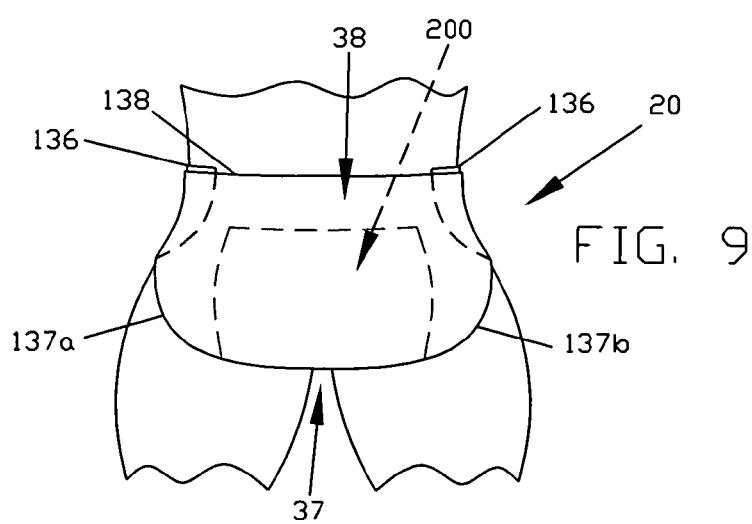
FIG. 9 is a back elevation view of the diaper 20 of FIG. 7.
Figure 10:
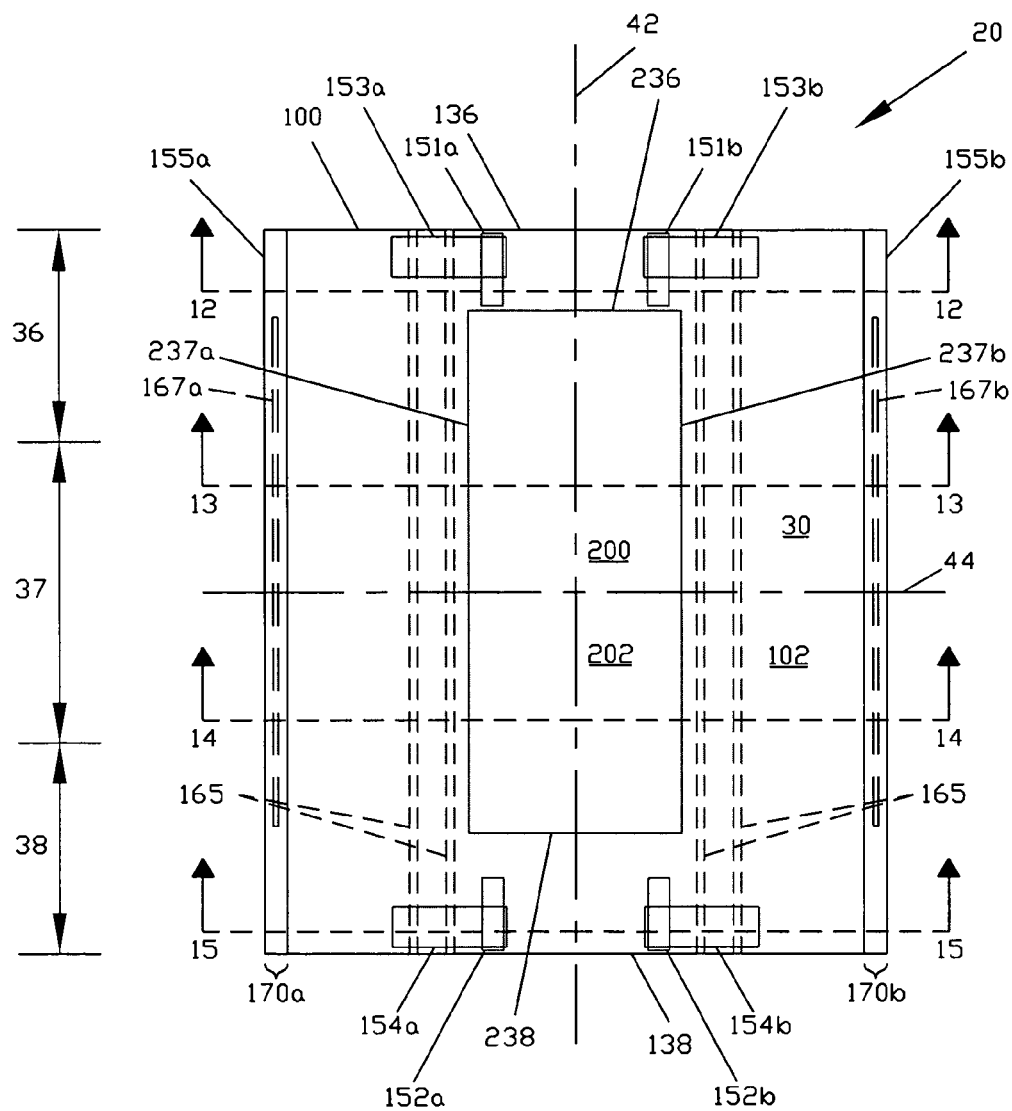
FIG. 10 is a plan view of an exemplary diaper 20 shown in its flat, uncontracted state, before the side flaps 147 are formed by folding portions of the chassis 100 laterally inward, i.e., toward the longitudinal axis 42.
Figure 11:
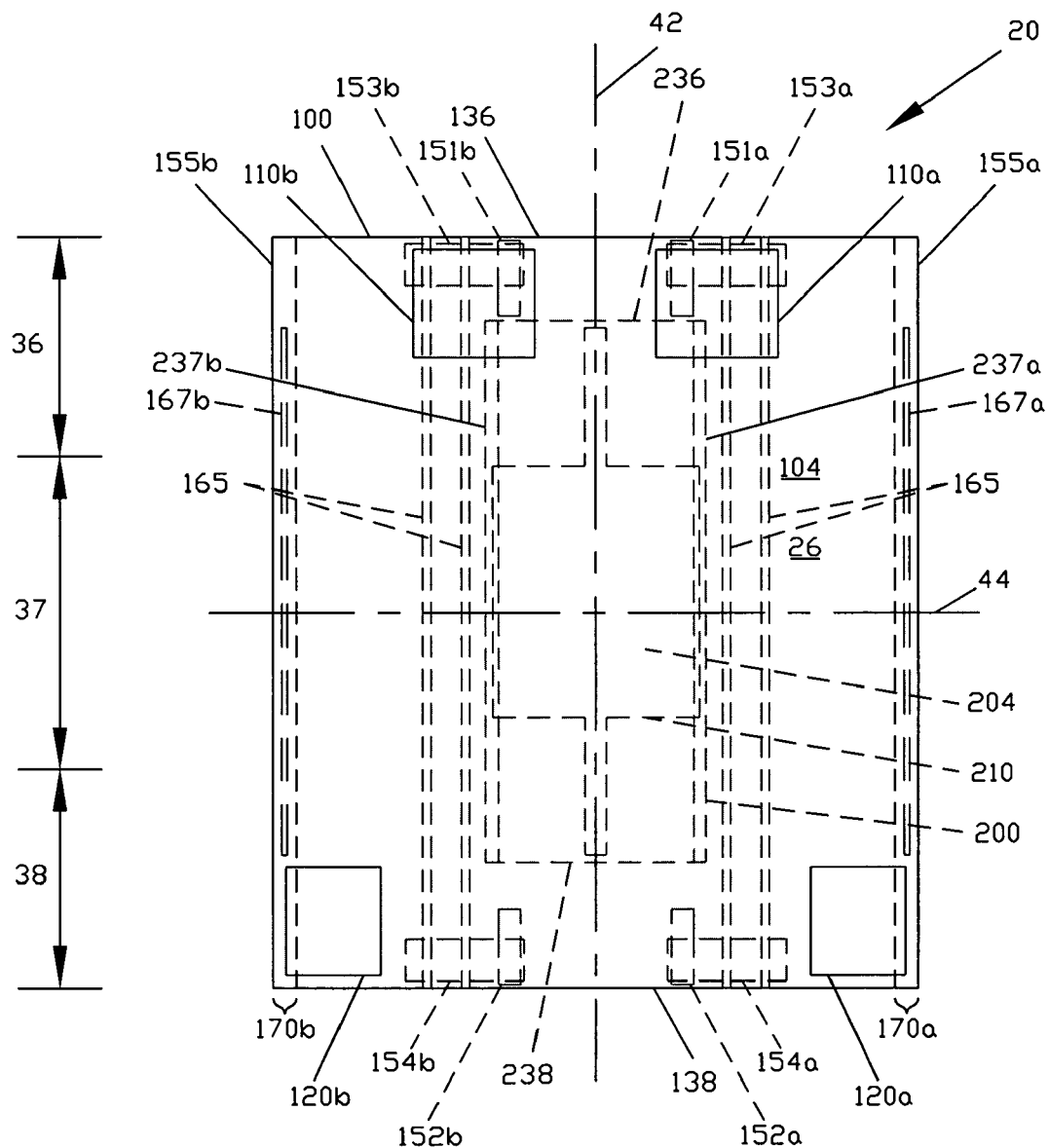
FIG. 11 is a plan view of the diaper 20 of FIG. 10 in its flat, uncontracted state, with the exterior portion of the diaper 20 shown facing the viewer.
Figure 12:
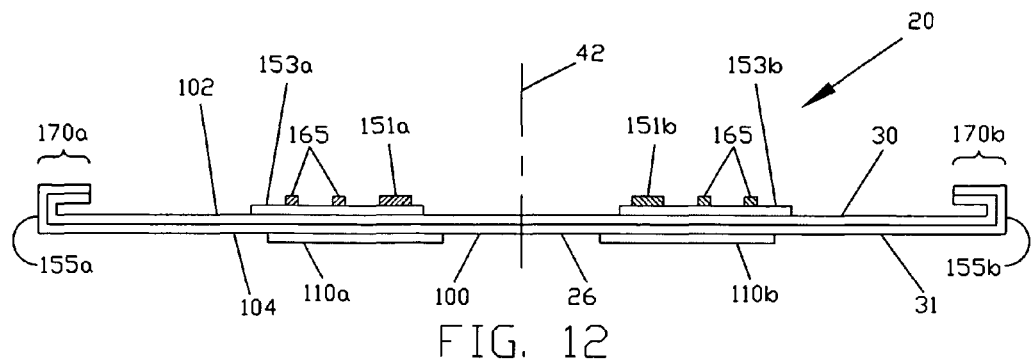
FIG. 12 is a section view of the diaper 20 of FIG. 10 taken at the section line 12-12.
Figure 13:
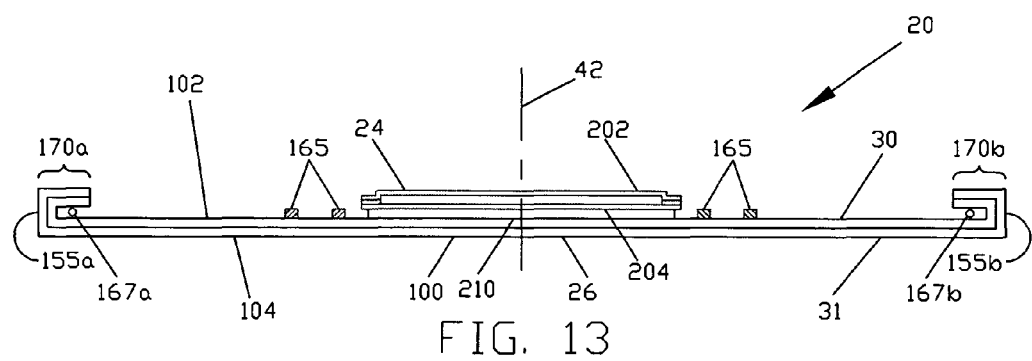
FIG. 13 is a section view of the diaper 20 of FIG. 10 taken at the section line 13-13.
Figure 14:
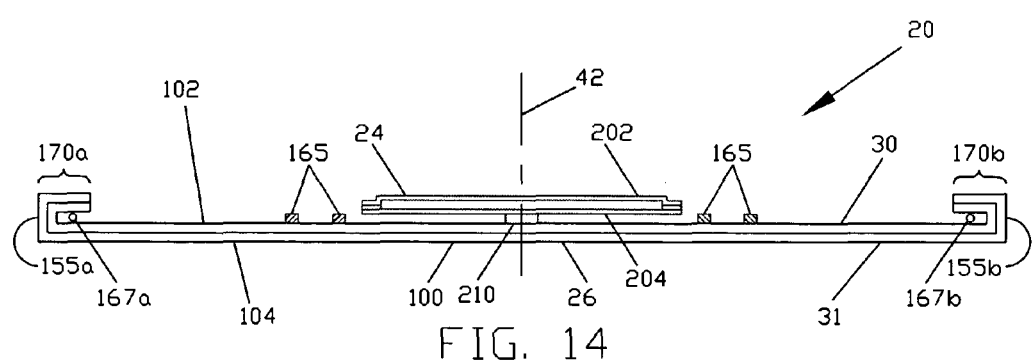
FIG. 14 is a section view of the diaper 20 of FIG. 10 taken at the section line 14-14.
Figure 15:
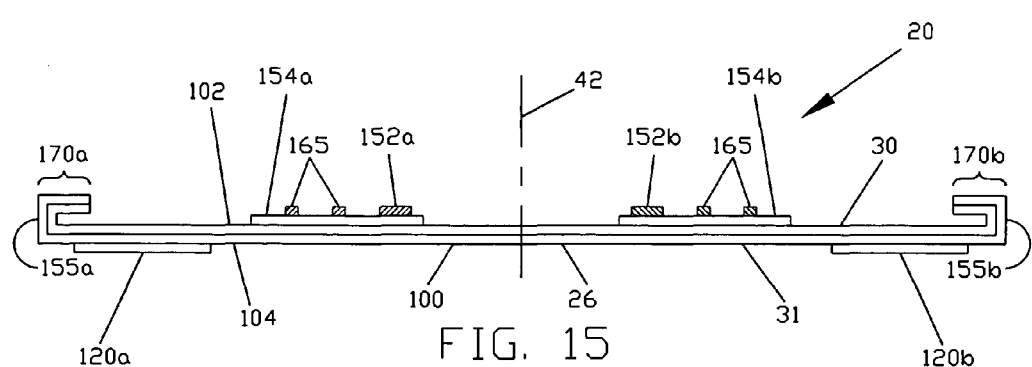
FIG. 15 is a section view of the diaper 20 of FIG. 10 taken at the section line 15-15.

In the finished diaper, the chassis has a generally "hourglass" shape, as in the exemplary diaper 20 shown in FIG. 1 and FIG. 2. Such a non-rectangular shape may be desirable in order to impart a tailored appearance to the diaper 20 when it is worn. Such a non-rectangular shape may also be desirable in order to impart an impression that the diaper 20 will fit comfortably between the legs of a wearer.

The chassis 100 is given the hourglass shape by the removal of laterally opposing portions of the chassis 100 from at least the crotch region 37, such as portions 142 shown in FIG. 17, to form laterally opposing side notches 139. This formation of the side notches 139 in the chassis makes its lateral dimension at and adjacent to the lateral axis 44 smaller than its lateral dimension at and adjacent to the front waist edge 136 and smaller than its lateral dimension at and adjacent to the back waist edge 138, i.e., makes the chassis narrower in the crotch region 37 than at the waist edges 136 and 138.

The contour of the side notch 139 that is formed by the removal of the side portion 142 at the cut side edge segment 135 is defined by the contour of that cut side edge segment. The contour may be continuously arcuate, as in the exemplary diapers 20 shown in FIG. 17, FIG. 18, FIG. 19, FIG. 20, and FIG. 21. Alternatively, the contour may be a composite formed by two longitudinally opposing arcuate portions 140 and a generally straight intermediate portion 141 connecting the arcuate portions, and thus not continuously arcuate, as in the exemplary diapers 20 shown in FIG. 1, FIG. 2, and FIG. 22. The side notches 139 may be disposed symmetrically with respect to either or both of the longitudinal axis 42 and the lateral axis 44 of the chassis 100. For example, the side notches 139 are shown disposed symmetrically with respect to both the longitudinal axis 42 and the lateral axis 44 in FIG. 1, FIG. 2, FIG. 17, FIG. 18, FIG. 19, FIG. 20, and FIG. 22. Alternatively, the side notches 139 may be disposed asymmetrically with respect to either or both of the longitudinal axis 42 and the lateral axis 44. For example, the side notches 139 are shown disposed symmetrically with respect to the longitudinal axis 42 and asymmetrically with respect to the lateral axis 44 in FIG. 21, where the side notches are offset toward the front waist edge 136.

The formation of the side notches 139 by the removal of the laterally opposing portions of the chassis leaves only longitudinally separated segments of the folded side edges 133 intact to prevent any bodily waste material from migrating laterally and escaping from the diaper 20. In particular, only the front folded side edge segments 133a and 133b and the back folded side edge segments 133c and 133d remain intact. The removal of the side portion 142 to form each side notch 139 detaches the respective side flap 147 from the underlying layer of the chassis along the contour of each cut side edge segment 135, thus creating an opening through which bodily waste material could escape. Therefore, the chassis 100 includes at least one longitudinally extending continuous side seal 165 disposed laterally proximally of each cut side edge segment 135. Each side flap 147 is attached to the underlying layer of the chassis 100 at the side seal 165. Each side seal 165 is water-impermeable at least laterally and thereby preferably acts as a dam to prevent the lateral escape of bodily waste material in the gap between the longitudinally separated front and back folded side edge segments.

A single side seal 165 may be used to attach each side flap 147 or, alternatively, two or more side seals 165 may be used to attach each side flap 147. For example, in the exemplary diaper 20 shown in FIG. 1 and FIG. 2, two laterally spaced side seals 165 are used to attach each side flap 147. As another example, a single side seal 165 is used to attach each side flap 147 in the exemplary diapers 20 shown in FIG. 17, FIG. 19, FIG. 20, FIG. 21, and FIG. 22. As yet another example, four laterally spaced side seals 165 are used to attach each side flap 147 in the exemplary diaper 20 shown in FIG. 18. The use of a single side seal 165 for each side panel 147 may help to minimize the cost of the diaper 20. On the other hand, the use of more than one side seal 165 for each side panel 147 may help to prevent the lateral escape of bodily waste materials in the event that one side seal is not perfectly continuous and thereby allows flow past itself.

The side seals 165 may be oriented generally parallel to the longitudinal axis 42 and to each other, as shown in FIG. 1, FIG. 2, FIG. 17, and FIG. 18. The side seals 165 may be configured as mirror images of each other, as shown most clearly in FIG. 19, FIG. 20, FIG. 21, and FIG. 22.

The side seals 165 may be formed by heat bonding, pressure bonding, a combination of heat bonding and pressure bonding, ultrasonic bonding, adhesive bonding, or in any other way or combination of ways known in the art for forming laterally water-impermeable bonds. Each side seal 165 may extend from the front waist edge 136 to the back waist edge 138, as shown in FIG. 1 and FIG. 2. Alternatively, a side seal 165 may extend less far in the longitudinal direction. For example, a side seal 165 may extend longitudinally only as far as the respective cut side edge segment 135 extends.

The side seals 165 may be formed when the chassis 100 is in the intermediate form shown in FIG. 17. Thus, a side seal 165 may initially extend through the side portion 142 of the chassis 100 that is eventually removed to form the side notch 139. Upon the removal of the side portion 142, such an initially longitudinally continuous side seal 165 may be made discontinuous, as shown in the finished exemplary diaper 20 of FIG. 1, FIG. 2, and FIG. 18. Alternatively, a side seal 165 may be formed laterally inwardly of the side portion 142 of the chassis 100 that is eventually removed to form the side notch 139 and thereby remain longitudinally continuous in the finished diaper. Exemplary side seals 165 remaining longitudinally continuous after the formation of the side notches 139 are also shown in the finished exemplary diaper 20 of FIG. 1 and FIG. 2.

Figure 20:
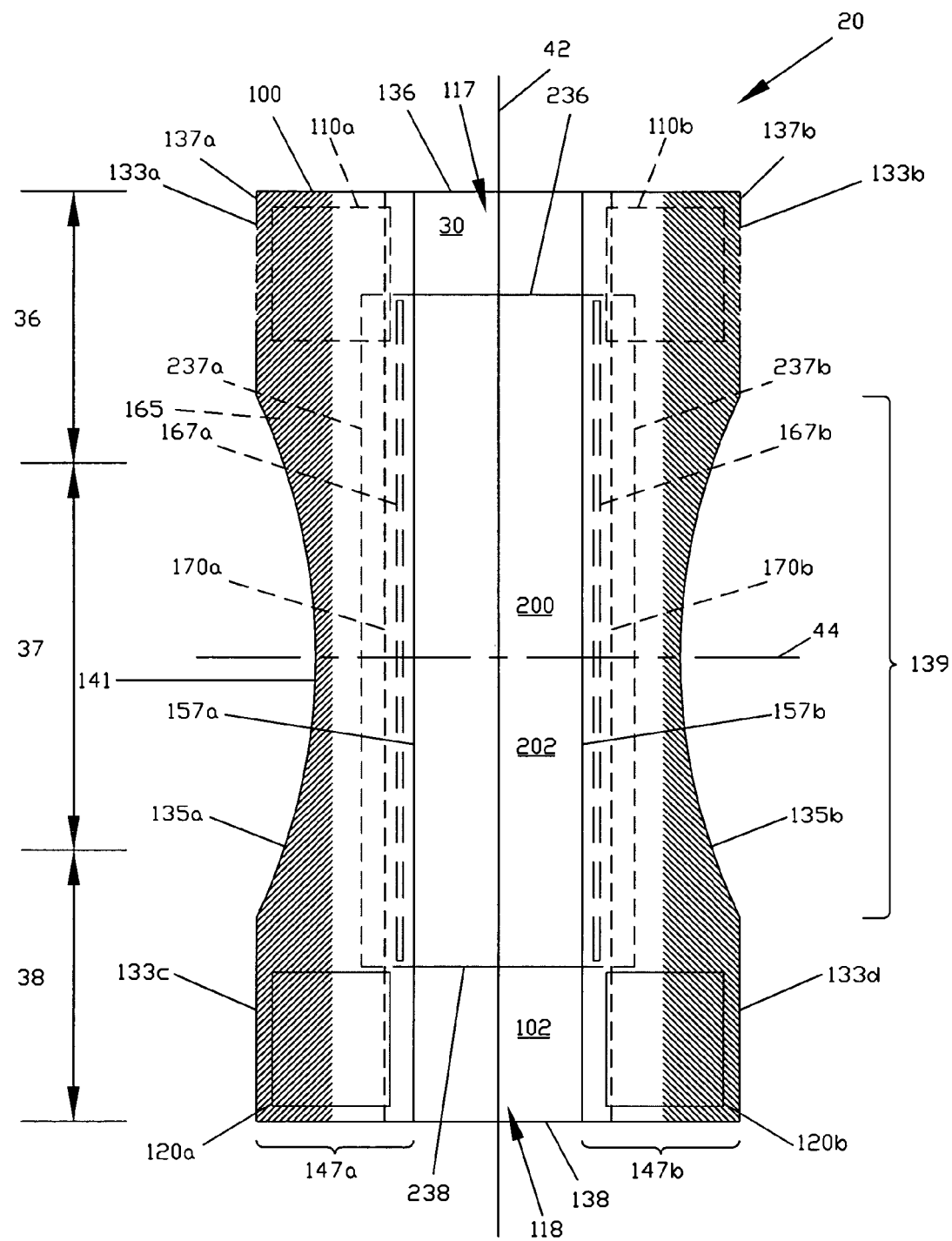
FIG. 20 is a plan view of another exemplary diaper 20 in its flat, uncontracted state, with the interior of the diaper 20 shown facing the viewer.
Figure 21:
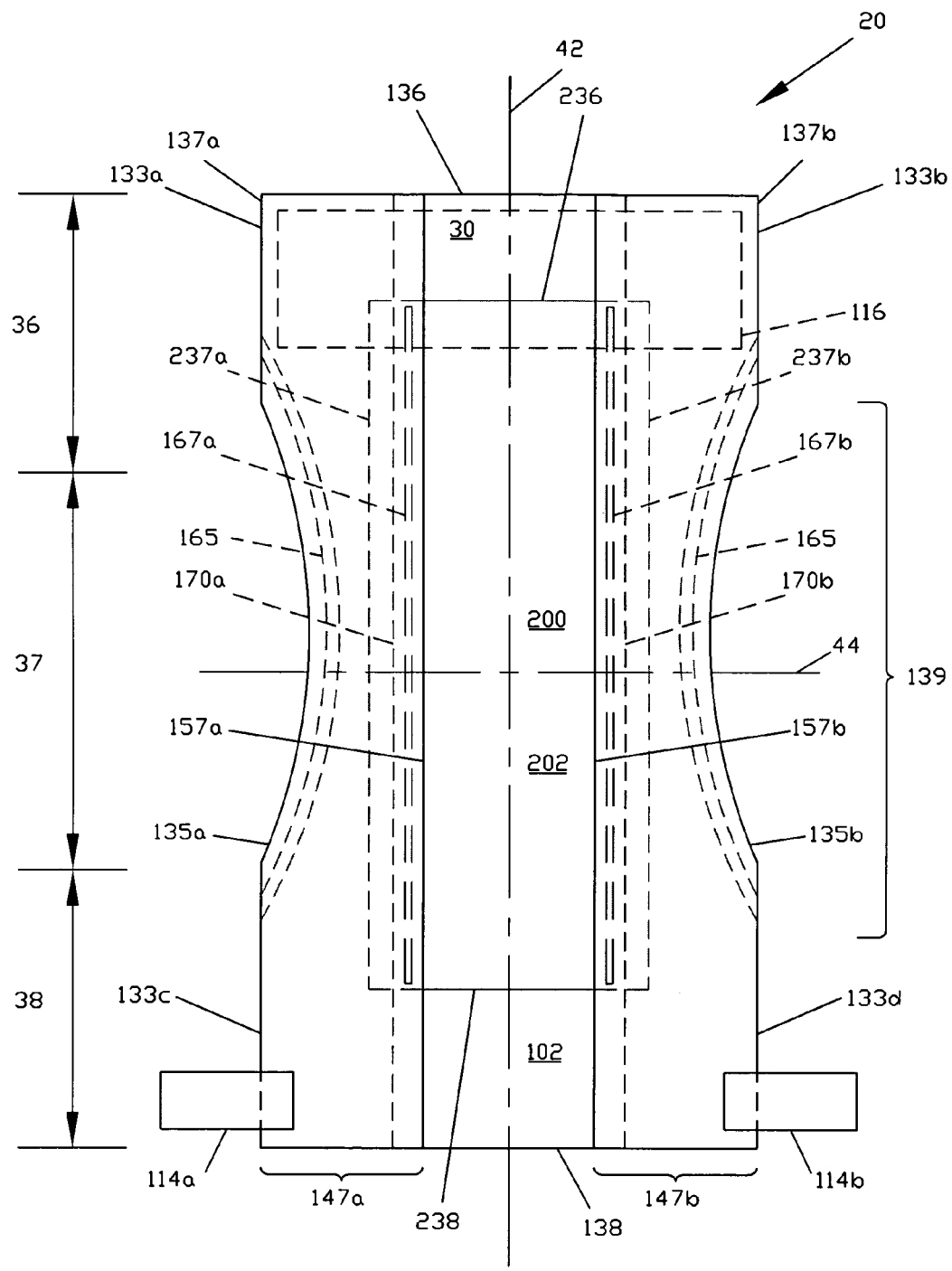
FIG. 21 is a plan view of another exemplary diaper 20 in its flat, uncontracted state, with the interior of the diaper 20 shown facing the viewer.
Figure 22:
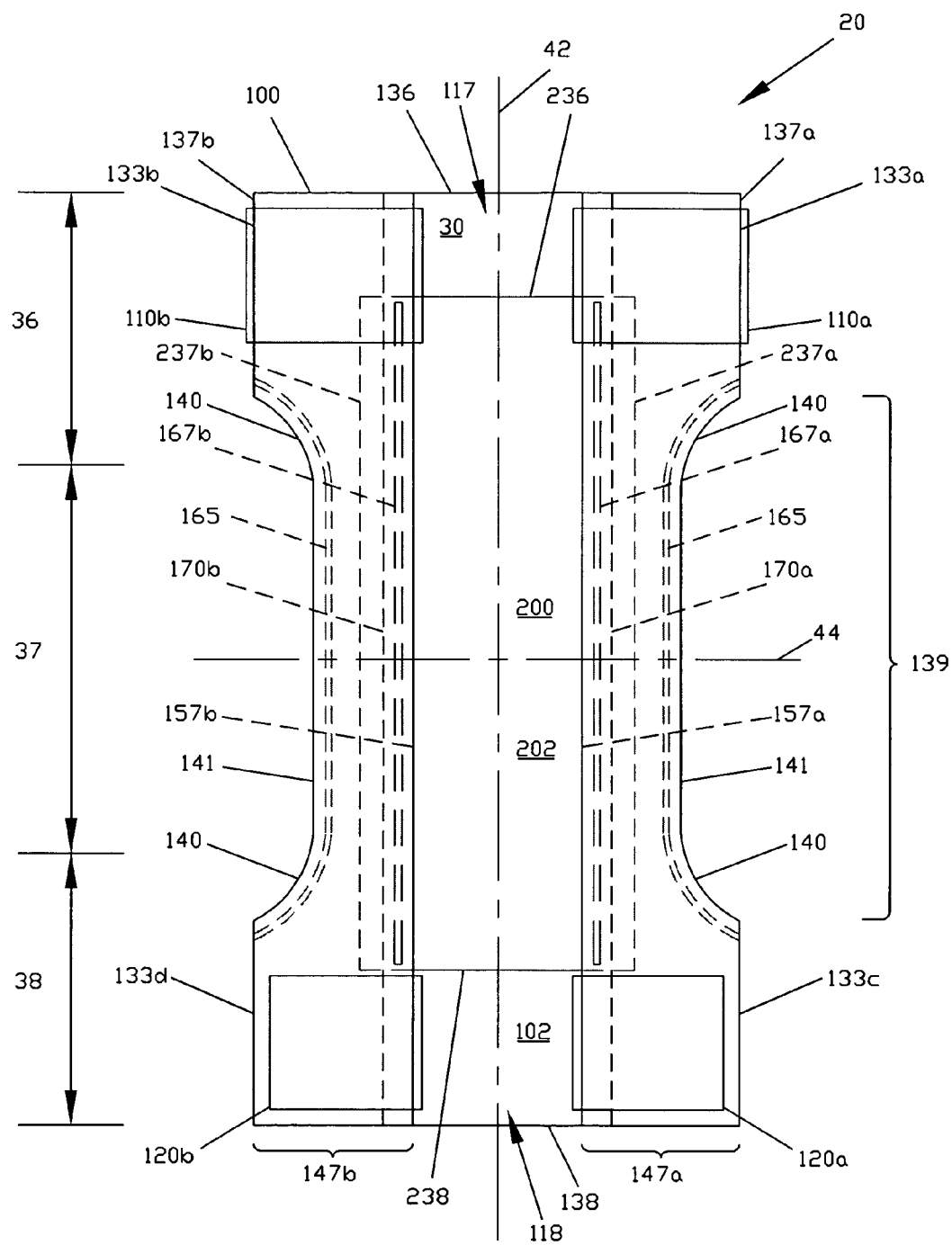
FIG. 22 is a plan view of another exemplary diaper 20 in its flat, uncontracted state, with the interior of the diaper 20 shown facing the viewer.

The side seals 165 may be substantially linear in form as shown in FIG. 1 and FIG. 2. Alternatively, a side seal 165 may be curvilinear in form. For example, as shown in FIG. 21 and FIG. 22, a side seal 165 may have a contour generally concentric to the contour of the cut side edge segment 135 and thereby "follow" the contour of the cut side edge segment from a point at or adjacent to a respective front folded side edge segment 133a or 133b to the respective corresponding back folded side edge segment 133c or 133d. In such a configuration, the combination of the front folded side edge segment, the side seal, and the back folded side edge segment may form a longitudinally continuous barrier to the lateral flow of bodily waste material between the front and back waist edges. As another alternative in which a combination of the front folded side edge segment, the side seal, and the back folded side edge segment may form a longitudinally continuous barrier to the lateral flow of bodily waste material, a side seal 165 may be sufficiently wide to extend from laterally inward of the cut side edge segment 135 to the folded side edge segments 133, such as the exemplary side seals shown in FIG. 19 and FIG. 20.

Each side seal 165 may be formed as a relatively narrow stripe being at least ten times as long as it is wide, such as the exemplary side seals shown in FIG. 1, FIG. 2, FIG. 10, FIG. 11, FIG. 12, FIG. 13, FIG. 14, FIG. 15, FIG. 17, FIG. 18, FIG. 21, and FIG. 22. Alternatively, each side seal 165 may be formed as a relatively wide band being less than ten times as long as it is wide, such as the exemplary side seals shown in FIG. 19 and FIG. 20.

A portion or the whole of the chassis 100 may be made extensible to a degree greater than the inherent extensibility of the material or materials from which the chassis is made. The additional extensibility may be desirable in order to allow the chassis 100 to conform to the body of a wearer during movement by the wearer. The additional extensibility may also be desirable, for example, in order to allow the user of a diaper 20 including a chassis 100 having a particular size before extension to extend the front waist region 36, the back waist region 38, or both waist regions of the chassis 100 to encircle the waist of an individual wearer whose waist circumference falls within a predefined range, i.e., to tailor the diaper to the individual wearer. Such extension of the waist region or regions may help to give the diaper a generally hourglass shape, so long as the crotch region 37 is extended to a relatively lesser degree than the waist region or regions, and may impart a tailored appearance to the diaper 20 when it is worn. In addition, the additional extensibility may be desirable in order to minimize the cost of the diaper. For example, an amount of material that would otherwise be sufficient only to make a relatively smaller diaper lacking this extensibility can be used to make a diaper capable of being extended to fit a wearer larger than the smaller diaper would fit. In other words, a lesser amount of material is needed in order to make a diaper capable of being properly fit onto a given size of a wearer when the material is made extensible as described. The portion of the chassis in one of the waist regions may be made laterally extensible to a maximum extensibility greater than a maximum extensibility of another portion of the chassis in the crotch region such that a lateral extension of each of the portions to its maximum extensibility imparts an hourglass shape to the chassis.

Additional extensibility in the chassis 100 in the lateral direction is relatively more useful than additional extensibility in the longitudinal direction because the abdomen of the wearer is likely to expand when the wearer changes posture from standing to sitting and the corresponding abdominal expansion increases the circumference that is encircled by the waist edges of the chassis 100, necessitating the lateral extension of the waist region or regions.

Figure 23:
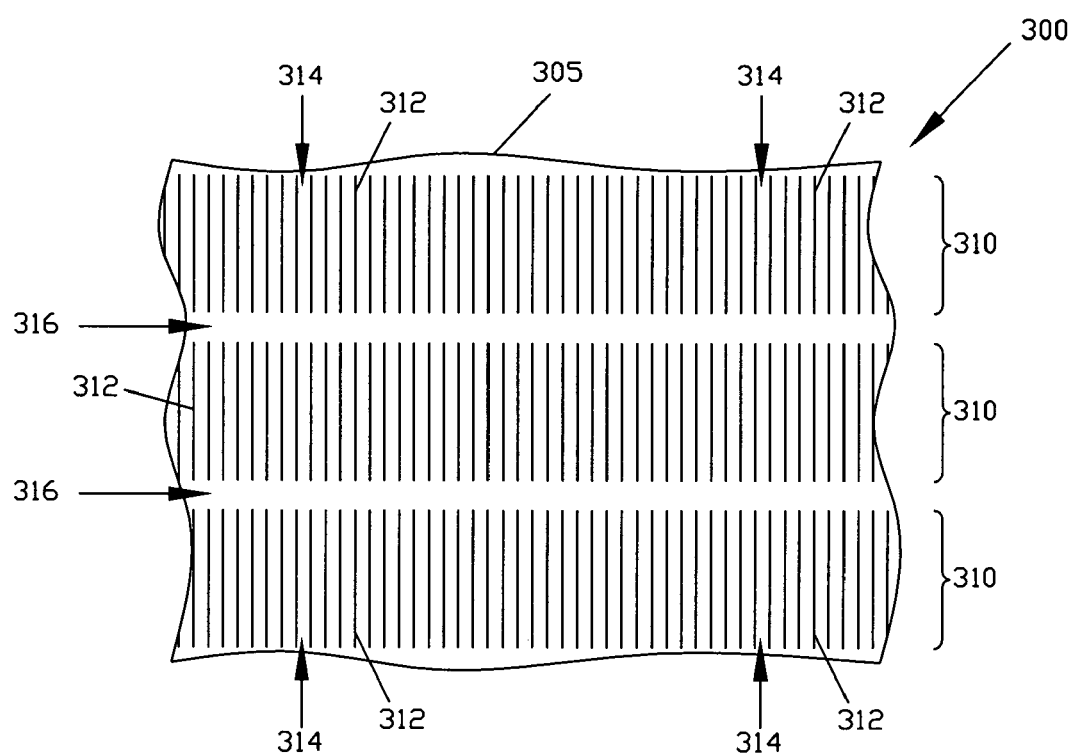
FIG. 23 is a plan view of an exemplary fragment of a formed web material.

Additional lateral extensibility in the chassis 100 may be provided in a variety of ways. For example, a material or materials from which the chassis 100 is made may be pleated by any of many known methods. Alternatively, all or a portion of the chassis may be made of a formed web material or a formed laminate of web materials like those described in U.S. Pat. No. 5,518,801 issued on 21 May 1996 in the name of Chappell et al. An exemplary fragment 300 of such a formed web material 305 is shown in FIG. 23. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

The front laterally central portion 117 and the back laterally central portion 118 of the chassis 100 between the attachment zones 151, 152, 153, and 154 where the side flaps 147 are attached to the interior surface 102 of the chassis adjacent to the respective waist edges 137 and 138 may have a different range of extensibility from the portions of the chassis in the attachment zones. Additionally or alternatively, the laterally central portions 117 and 118 may be extensible to a greater or lesser degree when subjected to a given level of opposing tensile forces, i.e., may be more easily or less easily extensible, than the portions of the chassis in the attachment zones. For example, if the chassis is made uniformly extensible across its entire width prior to the formation of the side flaps, the double layering in the areas of the attachment zones after the formation of the side flaps may have an effect of decreasing the degree of lateral extensibility of those areas under a given level of opposing tensile forces, such as by the side flaps acting as parallel "springs" that must be extended in order to extend the underlying attached portion of the chassis. As another example, the altered regions in the laterally central portions of the chassis may be deformed to a greater or a lesser degree than the altered regions in the attachment zones to render the laterally central portions more easily or less easily extensible than the respective portions in the attachment zones.

The front waist region 36 and the back waist region 38 can be fastened together to encircle the waist and the legs of the wearer in many well-known ways. For example, separate fastening devices such as safety pins, separate tapes, a separate tie strap or straps, and/or a separate belt can be used for this purpose. Alternatively or in addition, fastening elements can be incorporated into the chassis 100 to enable a user to apply the diaper 20 to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. These incorporated fastening elements may project laterally outward, i.e., away from the longitudinal axis 42 beyond one or both of the folded side edge segments 133 and/or may project longitudinally outward, i.e., away from the lateral axis 44 beyond one or both of the waist edges 136 and 138 or they may lie entirely inside the edges of the diaper 20. When a laminate backsheet is used and is oriented with the nonwoven disposed exteriorly, some forms of mechanical fasteners that typically require specific mating fastener elements, such as hooks that mate with loops, may be configured to engage with the nonwoven and thereby make the inclusion of the specific mating fastener element unnecessary.

Figure 18:
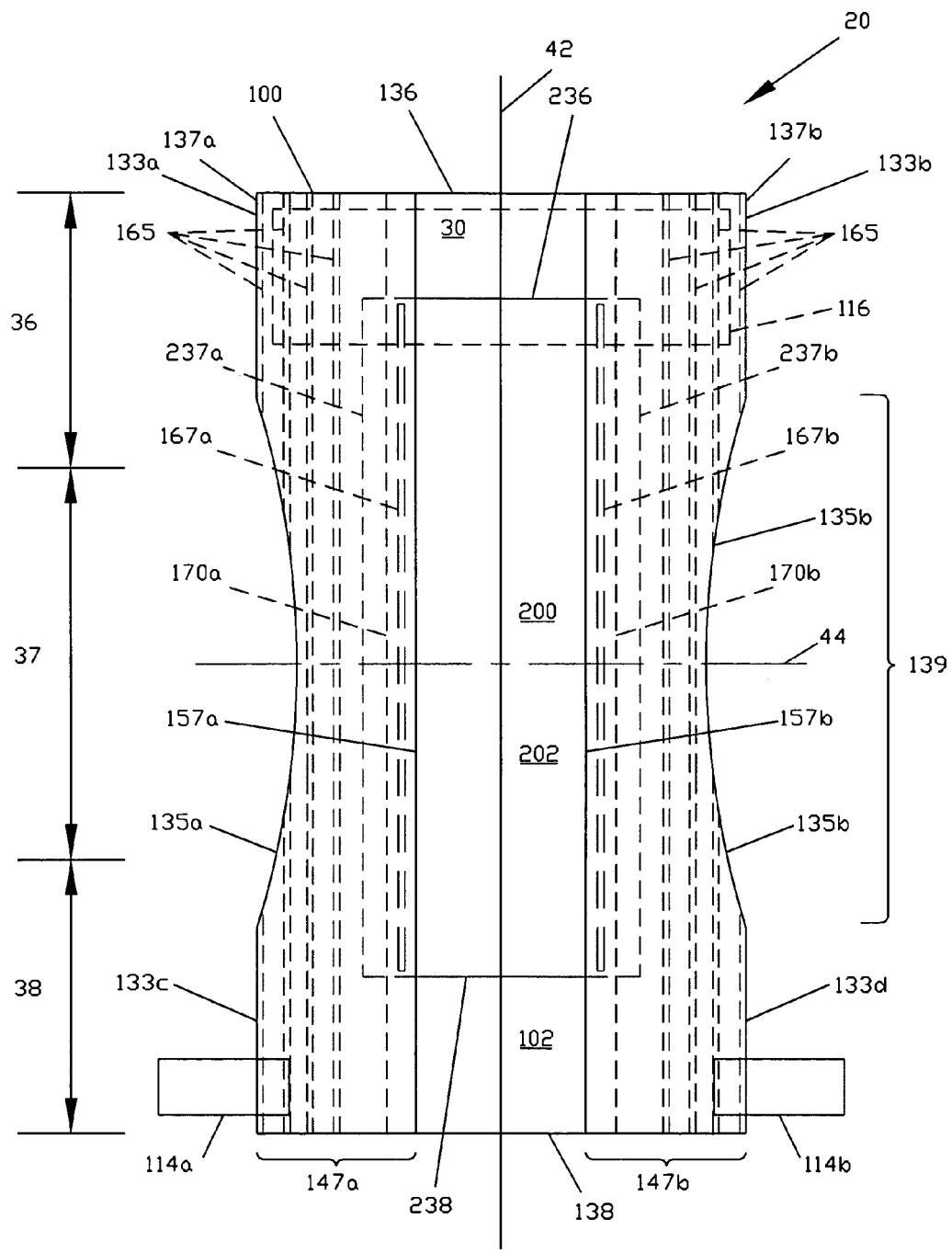
FIG. 18 is a plan view of another exemplary diaper 20 in its flat, uncontracted state, with the interior of the diaper 20 shown facing the viewer.

For example, as shown in FIG. 18 and FIG. 21, laterally opposing adhesive tape tabs 114a and 114b may be attached to the chassis 100 at or adjacent to the folded side edge segments 133 of the diaper 20. The adhesive tape tabs 114 shown in FIG. 18 and FIG. 21 project laterally outward from the respective folded side edge segments 133c and 133d in the back waist region 38. In use, the adhesive tape tabs 114a and 114b shown in FIG. 18 and FIG. 21 may be adhered to the exterior surface 104 of the chassis 100 in the front waist region 36 to fasten the back waist region 38 to the front waist region 36 in a back-over-front manner. Alternatively, similar adhesive tape tabs may be attached to the chassis 100 in the front waist region 36 and used to fasten the front waist region 36 to the back waist region 38 in a front-over-back manner. Suitable adhesive tapes are available from the 3M Corporation of St. Paul, Minn., U.S.A., under the designation of XMF99121.

Optionally, a fastening sheet 116 may be attached onto the exterior surface 104 of the chassis 100 in the front waist region 36 as shown in FIG. 18 and FIG. 21. The fastening sheet 116 shown in FIG. 18 and FIG. 21 lies entirely inside the edges of the diaper 20. Alternatively, two or more discrete fastening sheets may be attached onto the exterior surface of the chassis, instead of a single fastening sheet. For example, two laterally opposing fastening sheets may be attached in locations approximately corresponding to the left and right portions of the single fastening sheet 116. When a fastening sheet is provided, the adhesive tape tabs may be adhered to the fastening sheet to fasten the back waist region 38 and the front waist region 36 together. The fastening sheet may be formed of a material used elsewhere in the diaper, such as a film or a nonwoven. In embodiments in which the chassis is extensible, it is preferred that any fastening sheet also be extensible such that the fastening sheet will not restrict the extensibility of the portion of the chassis onto which it is attached. For example, an extensible nonwoven may be used for the fastening sheet. The fastening sheet serves to distribute the tensile force transmitted by each of the adhesive tape tabs over an area of the backsheet 26 that is larger than the adhered area of the adhesive tape tab. In addition, when a single fastening sheet such as the fastening sheet 116 in FIG. 18 and FIG. 21 is used, the fastening sheet may, itself, bear a portion of the tensile force between the laterally opposing adhesive tape tabs and thereby relieve a portion of the force exerted on the backsheet. Thus, the incorporation of such a fastening sheet may be desirable, for example, in order to make it possible to use a relatively inexpensive and relatively weak material for the backsheet 26. The fastening sheet may be formed of a material having greater strength than the backsheet. Such a stronger material may be more expensive per unit area than the backsheet, but the fastening sheet may be relatively smaller than the backsheet. Therefore, the total cost of a diaper having a fastening sheet may be less than the total cost of a diaper having a backsheet having sufficient strength for adhesive tape tabs to be adhered directly to the exterior surface of the backsheet.

Figure 19:
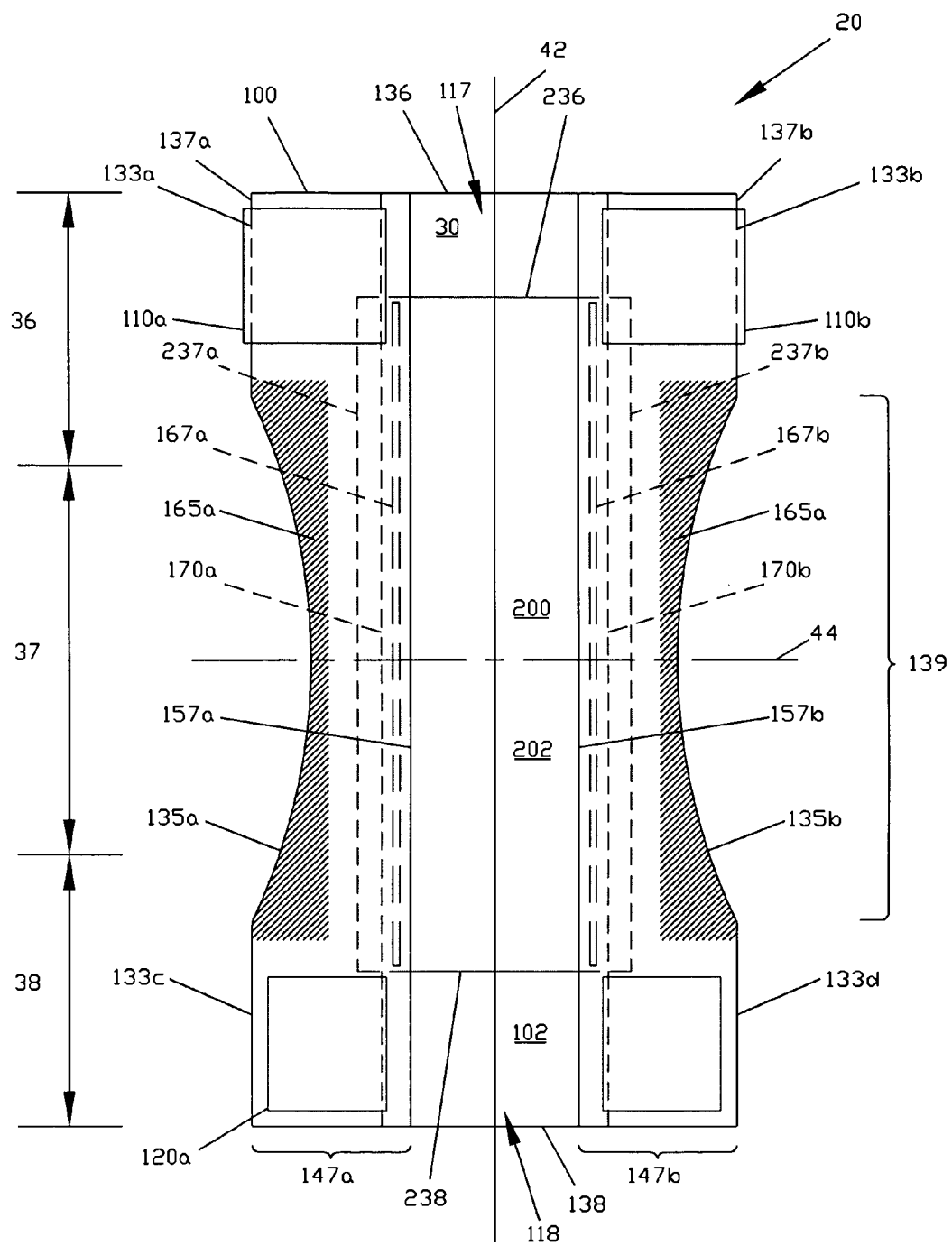
FIG. 19 is a plan view of another exemplary diaper 20 in its flat, uncontracted state, with the interior of the diaper 20 shown facing the viewer.

As another example, cohesive fastening elements may be used. Exemplary fastening elements in the form of cohesive fastening patches may be formed of an inherently crystalline water-based synthetic elastomer to which a tackifying agent has been added to disrupt the polycrystalline structure and thereby render the elastomer cohesive. Such synthetic cohesive products are available from Andover Coated Products, Incorporated, of Salisbury, Mass., U.S.A. and are described in U.S. Pat. No. 6,156,424 issued on 5 Dec. 2000 in the name of Taylor. Cohesive fastening patches may be disposed on the exterior and/or interior surfaces of the chassis in arrangements that allow exclusively for either back-over-front fastening or front-over-back fastening of the waist regions together. Alternatively, the cohesive fastening patches may be disposed in a reversible configuration that is adapted to provide the user of the diaper with both options for fastening, i.e., either back-over-front or front-over-back, in the same diaper, according to personal preference. Suitable configurations of cohesive fastening elements are disclosed in U.S. patent application Ser. No. 10/770,043 filed on 2 Feb. 2004. Exemplary configurations of front cohesive fastening patches 110 and back cohesive fastening patches 120 are also shown in FIG. 19, FIG. 20, and FIG. 22.

Description of the Absorbent Assembly

Figure 24:
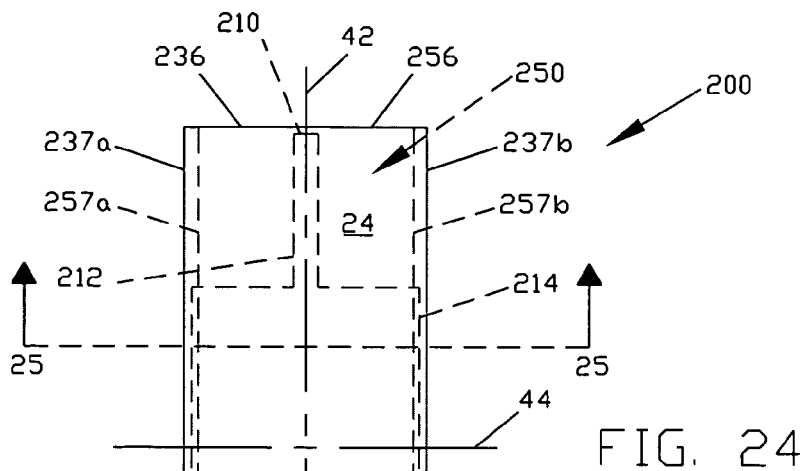
FIG. 24 is a plan view of an exemplary absorbent assembly 200 with the interior of the absorbent assembly 200 shown facing the viewer.
Figure 25:
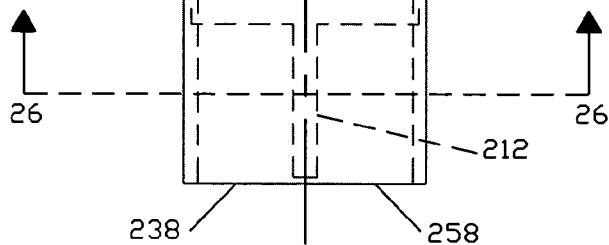
FIG. 25 is a view of the absorbent assembly of FIG. 29 taken at the section line 25-25.
Figure 26:
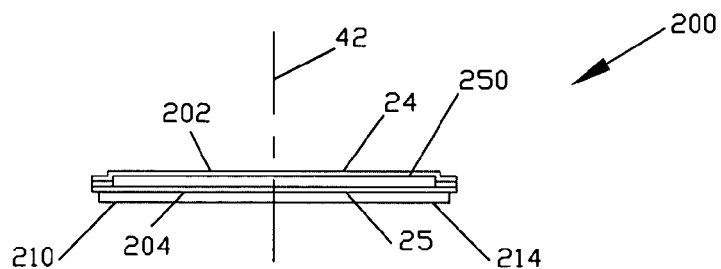
FIG. 26 is a view of the absorbent assembly of FIG. 29 taken at the section line 26-26.

As shown in FIG. 24, FIG. 25, and FIG. 26, the absorbent assembly 200 includes an absorbent core 250 that serves to absorb and retain liquid bodily waste materials. The absorbent core 250 has a laterally extending front edge 256 and a longitudinally opposing and laterally extending back edge 258. The absorbent core 250 also has a longitudinally extending left side edge 257*a* and a laterally opposing and longitudinally extending right side edge 257*b*, both absorbent core side edges extending longitudinally between the front edge 256 and the back edge 258. The absorbent core 250 also has an interior surface 252 and an exterior surface 254.

The absorbent assembly 200 may be attached to the interior surface 102 of the chassis 100 over any part or the whole of the area of the absorbent assembly 200. Preferably, the absorbent assembly 200 is attached on its exterior surface 204 to the chassis 100 in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence. Alternatively, the cruciform attachment pattern may include detached portions and thereby lack contiguity but still be arranged such that the shape of the overall pattern is a cruciform. For example, a discontiguous cruciform attachment pattern may include a longitudinally extending portion disposed along the longitudinal axis and separate left and right laterally distal portions disposed along or adjacent to the lateral axis and thereby form a cruciform as the shape of the overall pattern.

Exemplary contiguous cruciform attachment patterns 210 are shown in FIG. 11, FIG. 24, FIG. 25, and FIG. 26. The portions of the chassis 100 that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in these figures leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in these figures prevents the portion of the chassis 100 in the crotch region 37 to which the absorbent assembly 200 is attached from shifting relative to the absorbent assembly 200 in that region. A relatively wide laterally extending portion 214 of a cruciform attachment pattern 210 may also contribute to the effectiveness and positioning of the side flaps 147 when the elastic strands 167 lift the proximal edges 157 into contact with the body of the wearer. For example, if the absorbent assembly was attached only along the longitudinal centerline, the absorbent assembly could be compressed by the legs to a smaller lateral dimension than desired. This narrowing of the absorbent assembly would in turn allow the chassis 100 in the crotch region 37 to narrow, i.e., allow the side edges 137 to move toward the longitudinal axis 42. Such narrowing of the chassis 100 would increase the likelihood that the side flaps 147 would distort and fail to maintain contact with the body and/or become improperly positioned. However, because the relatively wide laterally extending portion 214 of the cruciform attachment pattern 210 restrains the chassis 100 over a relatively wide portion of the width of the crotch region 37, the side flaps 147 are more likely to remain properly positioned while being lifted by the elastic strands 167.

Within the extent of the cruciform attachment pattern 210, the absorbent assembly 200 may be attached to the chassis 100 continuously or intermittently. For example, a film of an adhesive may be applied continuously over the entire area of the cruciform attachment pattern and then used to continuously attach the absorbent assembly to the chassis. As an alternative example, an adhesive may be applied discontinuously at and inside the boundaries of the cruciform attachment pattern, such as in the form of dots, stripes, beads, spirals, etc., and then used to attach the absorbent assembly to the chassis.

The cruciform attachment pattern 210 may be disposed symmetrically with respect to either or both of the longitudinal axis 42 and the lateral axis 44 of the chassis 100. Alternatively, the cruciform attachment pattern 210 may be disposed asymmetrically with respect to either or both of the longitudinal axis 42 and the lateral axis 44. In addition, the cruciform attachment pattern 210 may be disposed symmetrically with respect to either or both of the side edges 237 and the front edge 236 and the back edge 238 of the absorbent assembly 200. Alternatively, the cruciform attachment pattern 210 may be disposed asymmetrically with respect to either or both of the side edges 237 and front edge 236 and back edge 238.

Suitable configurations of cruciform attachment patterns are disclosed in U.S. patent application Ser. No. 10/880,128 filed on 29 Jun. 2004.

The absorbent core 250 may be disposed between a lower covering sheet that is disposed on the exterior face of the absorbent core 250 and an upper covering sheet that is disposed on the interior face of the absorbent core 250. Such an upper covering sheet and lower covering sheet may be attached together to contain the absorbent core 250 between them and thereby form the absorbent assembly 200. For example, an upper covering sheet and a lower covering sheet may be attached together at or adjacent to the side edges 237 of the absorbent assembly 200. Alternatively, an upper covering sheet and a lower covering sheet may be attached together in places other than the side edges 237, e.g., at or adjacent to the end edges 236 and 238 of the absorbent assembly 200, or at or adjacent to both the end edges 236 and 238 and the side edges 237. Both the upper covering sheet and the lower covering sheet are water vapor-permeable, i.e., breathable.

The upper covering sheet 24 is water-permeable and allows liquid bodily waste to pass through to the absorbent core 250, where the liquid bodily waste is absorbed. The lower covering sheet 25 may be water-impermeable. However, the lower covering sheet 25 preferably is water-permeable. In embodiments in which both the upper covering sheet 24 and the lower covering sheet 25 are water-permeable, any liquid bodily waste that is deposited onto the upper covering sheet 24 but does not pass through the upper covering sheet 24 to the absorbent core 250 can flow around an edge of the absorbent assembly 200 to reach the lower covering sheet 25 and then pass through the lower covering sheet 25 to the absorbent core 250.

The upper covering sheet 24 may form the interior surface 202 of the absorbent assembly 200 that is intended to be placed against the body of the wearer. The upper covering sheet 24 preferably is formed of a soft material that will not irritate the skin of the wearer. Many materials that are suitable for a water-permeable covering sheet are well-known in the art, including synthetic nonwovens such as spunbonded or carded polypropylene, polyester, or rayon. Likewise, many materials that are suitable for a covering sheet that is water-impermeable are well-known in the art, including the materials that are suitable for the backsheet 26.

The upper covering sheet 24 and the lower covering sheet 25 may extend to the same width and the same length. Alternatively, one or more of the edges of one of the covering sheets may lie distally relative to the respective edge or edges of the other covering sheet. For example, the upper covering sheet may extend longitudinally only to an extent sufficient to cover the absorbent core and the lower covering sheet may extend longitudinally beyond the upper covering sheet toward or to the adjacent waist edge. Such an extended covering sheet may serve to isolate the skin of the wearer from a portion of the backsheet 26 as may be desirable, for example, when the diaper 20 is worn under conditions in which contact between the skin and a backsheet film could be uncomfortable.

The absorbent core 250 includes a storage component 272 that serves to absorb and retain liquid bodily waste materials. Suitable known materials for the absorbent core storage component include cellulose fibers in the form of comminuted wood pulp, commonly known as "airfelt", natural or synthetic fibrous materials, and superabsorbent polymers, used either singly or in mixtures and commonly formed into layers or sheets, etc. These absorbent materials may be used separately or in combination. Many known absorbent materials may be used in a discrete form, i.e., in the form of fibers, granules, particles, and the like. Such a discrete form of an absorbent material may be immobilized by an adhesive that attaches the discrete pieces together to form a coherent layer or that attaches the discrete pieces to a substrate layer or that attaches the discrete pieces both to each other and to the substrate layer.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. For example, the acquisition component may be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materials are more fully described in U.S. Pat. No. 4,950,264 issued to Osborn on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Figure 27:
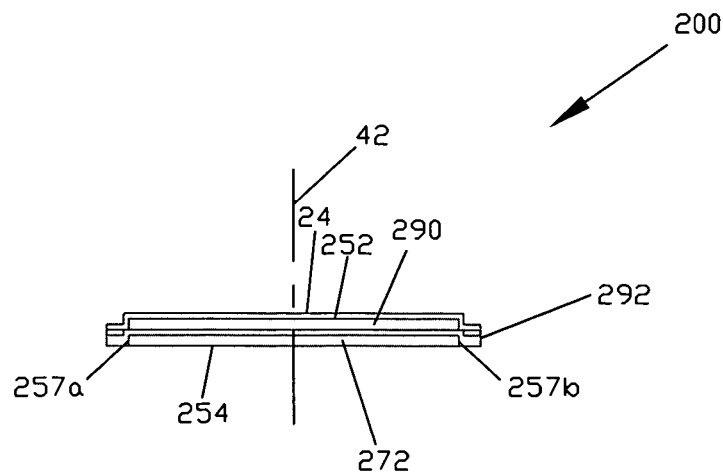
FIG. 27 is a section view of an exemplary absorbent assembly 200.

Such an absorbent core acquisition component 290 is shown overlying the absorbent core storage component 272 in FIG. 27. A separation sheet 292 of, e.g., a tissue or a nonwoven material, may be disposed between the absorbent core storage component 272 and the absorbent core acquisition component 290 to help ensure that none of the gel formed by a superabsorbent polymer that may be included in the absorbent core storage component reaches the skin of the wearer. This separation sheet 292 may extend laterally beyond the side edges 257 of the absorbent core 250 and the upper covering sheet 24 may be attached to the separation sheet 292. In this arrangement, the liquid bodily waste material that is deposited onto the upper covering sheet 24 will pass through the thickness of the upper covering sheet 24 to be absorbed by the absorbent core acquisition component 290, and some or all of it may then pass through the thickness of the separation sheet 292 and then be absorbed and retained by the absorbent core storage component 272.

Figure 28:
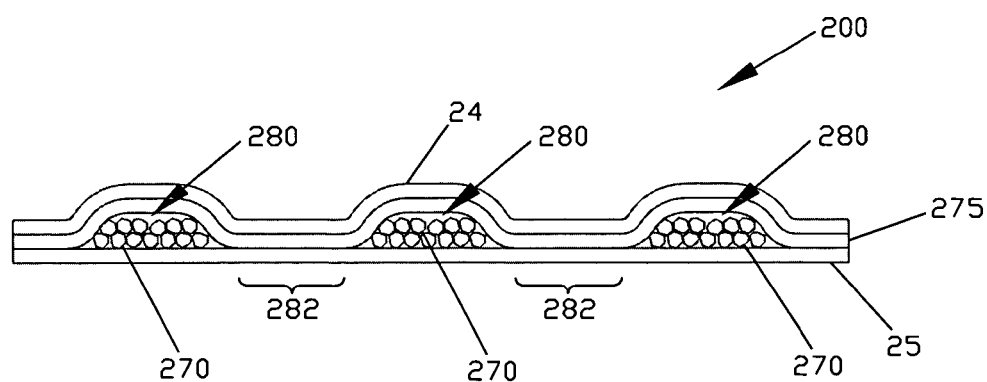
FIG. 28 is a section view of an exemplary absorbent assembly 200.

In some exemplary embodiments, an absorbent core storage component may include the discrete form of an absorbent material that is immobilized in pockets formed by a layer of a thermoplastic material, such as a hot melt adhesive, that intermittently contacts and adheres to a substrate sheet, while diverging away from the substrate sheet at the pockets. Absorbent core components having such structures and being suitable for the storage of liquid bodily wastes are described in U.S. patent applications Ser. Nos. 10/776,839 and 10/776,851, both filed on 11 Feb. 2004 in the name of Ehrnsperger et al. An exemplary absorbent core storage component 272 having such a structure is shown in FIG. 28. In this absorbent core storage component 272, particles 270 of a superabsorbent polymer are contained inside pockets 280 formed by a layer 275 of a thermoplastic material. The absorbent core storage component may include both particles of superabsorbent polymer and airfelt and both materials may be contained inside the pockets formed by the layer of the thermoplastic material. Alternatively as shown in FIG. 28, an exemplary absorbent core storage component may contain no airfelt and therefore the component can be made relatively thinner and more flexible for the comfort of the wearer. In addition, the particles of the superabsorbent polymer can be immobilized relatively more easily in the absence of airfelt. As shown in FIG. 28, the layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 may have the form of a sheet of fibers of the thermoplastic material through which the liquid bodily waste may pass to the particles to be absorbed by the particles 270 of the superabsorbent polymer.

In FIG. 28, a separate thermoplastic layer covering sheet 276 is shown overlying the layer 275 of the thermoplastic material. Alternatively, the separate thermoplastic layer covering sheet 276 may be omitted. As another alternative, two absorbent core storage components each like that shown in FIG. 28 except for the omission of the thermoplastic layer covering sheet 276 may be superposed with one absorbent core storage component inverted such that the respective substrate sheets distally oppose each other. In such a combination of absorbent core storage components, either or both of the distally opposing substrate sheets may serve respectively as either or both of an upper covering sheet and a lower covering sheet for the absorbent assembly. Alternatively, the absorbent assembly may include a separate lower covering sheet and/or a separate upper covering sheet.

Statements of Incorporation by Reference and Intended Scope of Claims

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention.

While particular embodiments and/or individual features of the present invention have been described herein, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable diaper comprising:
    an absorbent assembly comprising an absorbent core;
    a chassis having a longitudinal axis, a lateral axis, a front waist region having a front waist edge, a back waist region having a back waist edge, a crotch region between the waist regions, laterally opposing side edges extending between the front waist edge and the back waist edge, an exterior surface, and an interior surface;
    the chassis comprising a water-impermeable backsheet and laterally opposing longitudinally extending side flaps formed at least in part by laterally inwardly folded portions of the backsheet, the laterally inwardly folded portions of the backsheet extending from the front waist edge to the back waist edge, the laterally opposing longitudinally extending side flaps extending from the front waist edge to the back waist edge;
    each of the side flaps having a proximal edge and longitudinally opposing ends and a longitudinally extending elastic gathering member attached adjacent to the proximal edge;
    each of the side flaps being attached to at least one of the chassis and absorbent assembly adjacent to its longitudinally opposing ends of the side flap and also comprising at least one longitudinally extending side seal disposed between its proximal edge of the side flap and the respective side edge of the chassis; and
    the chassis having laterally opposing side notches in at least the crotch region forming a non-rectangular shape.

2. The disposable diaper of claim 1 wherein each side seal is water-impermeable at least laterally.

3. The disposable diaper of claim 1 wherein each side edge is formed of a front folded side edge segment in the front waist region where the backsheet is folded laterally inward, a back folded side edge segment in the back waist region where the backsheet is folded laterally inward, and a cut side edge segment defining the side notch and connecting the front folded side edge segment and the back folded side edge segment.

4. The disposable diaper of claim 3 wherein the side seal is continuous from the front folded side edge segment to the back folded side edge segment such that the front folded side edge segment and the back folded side edge segment and the side seal together form a longitudinally continuous barrier to a lateral flow of bodily waste material between the front waist edge and the back waist edge.

5. The disposable diaper of claim 1 wherein the side seal extends from the front waist edge to the back waist edge.

6. The disposable diaper of claim 1 wherein the side seal extends longitudinally less far than from the front waist edge to the back waist edge.

7. The disposable diaper of claim 1 wherein the side seal is substantially linear in form.

8. The disposable diaper of claim 1 wherein the side seal is an adhesive bond.

9. The disposable diaper of claim 1 wherein the side seal is at least ten times as long as the side is wide.

10. The disposable diaper of claim 1 wherein each side edge is formed of a front folded side edge segment in the front waist region where the backsheet is folded laterally inward, a back folded side edge segment in the back waist region where the backsheet is folded laterally inward, and a cut side edge segment defining the side notch and connecting the front folded side edge segment and the back folded side edge segment, and the side seal is less than ten times as long as the side seal is wide and the side seal extends from laterally inward of the cut side edge segment to each of the folded side edge segments.

11. A disposable diaper comprising:
    an absorbent assembly comprising an absorbent core;
    a chassis having a longitudinal axis, a lateral axis, a front waist region having a front waist edge, a back waist region having a back waist edge, a crotch region between the waist regions, laterally opposing side edges extending between the front waist edge and the back waist edge, an exterior surface, and an interior surface;
    the chassis comprising a water-impermeable backsheet and laterally opposing longitudinally extending side flaps formed at least in part by laterally inwardly folded portions of the backsheet, the laterally inwardly folded portions of the backsheet extending from the front waist edge to the back waist edge, the laterally opposing longitudinally extending side flaps extending from the front waist edge to the back waist edge;
    each of the side flaps having a proximal edge and longitudinally opposing ends and a longitudinally extending elastic gathering member attached adjacent to the proximal edge;

each of the side flaps being attached adjacent to the longitudinally opposing ends to the interior surface; each of the side flaps also being attached to the interior surface of at least one longitudinally extending side seal disposed between the proximal edge and the respective side edge of the chassis; and the chassis having a non-rectangular shape having laterally opposing side notches in at least the crotch region.

12. The disposable diaper of claim 11 wherein each of the side notches has a continuously arcuate contour.

13. The disposable diaper of claim 11 wherein each of the side notches has a contour formed by longitudinally opposing arcuate portions and a generally straight intermediate portion connecting the arcuate portions.

14. The disposable diaper of claim 11 wherein each side edge is formed of a front folded side edge segment in the front waist region where the backsheet is folded laterally inward, a back folded side edge segment in the back waist region where the backsheet is folded laterally inward, and a cut side edge segment defining the side notch and connecting the front folded side edge segment and the back folded side edge segment.

15. A disposable diaper comprising:

an absorbent assembly comprising an absorbent core;

a chassis having a longitudinal axis, a lateral axis, a front waist region having a front waist edge, a back waist region having a back waist edge, a crotch region between the waist regions, laterally opposing side edges extending between the front waist edge and the back waist edge, an exterior surface, and an interior surface to which the absorbent assembly is attached, the chassis comprising a water-impermeable backsheet and laterally opposing longitudinally extending side flaps formed at least in part by laterally inwardly folded portions of the backsheet, the laterally inwardly folded portions of the backsheet extending from the front waist edge to the back waist edge, the laterally opposing longitudinally extending side flaps extending from the front waist edge to the back waist edge;

each of the side flaps having a proximal edge and longitudinally opposing ends and a longitudinally extending elastic gathering member attached adjacent to the proximal edge;

each of the side flaps being attached adjacent to the longitudinally opposing ends to the interior surface such that when allowed to relax, the elastic gathering member contracts and lifts the proximal edge away from the interior surface of the absorbent assembly, thereby raising the side flap to form a side barrier;

each of the side flaps also being attached at least one longitudinally extending side seal disposed between its proximal edge and the respective side edge of the chassis; and the chassis having a non-rectangular shape having laterally opposing side notches in at least the crotch region.

16. The disposable diaper of claim 1 wherein the absorbent assembly is attached to the interior surface of the chassis.

17. The disposable diaper of claim 11 wherein the elastic gathering member, such when allowed to relax, contracts and lifts the proximal edge away from the interior surface of the absorbent assembly, thereby raising the side flap to form a side barrier.

18. The disposable diaper of claim 15 wherein the side seal is water-impermeable, at least laterally.

* * * * *

UNITED STATES PATENT AND TRADEMARK OFFICE
CERTIFICATE OF CORRECTION

PATENT NO. : 8,187,239 B2
APPLICATION NO. : 11/140888
DATED : May 29, 2012
INVENTOR(S) : Gary Dean LaVon Page 1 of 1

It is certified that error appears in the above-identified patent and that said Letters Patent is hereby corrected as shown below:

Column 18
Line 5, delete "-its-" and insert -- the --.

Line 36, after the word "side" insert -- seal --.

Column 19
Line 2, delete "each of the side flaps also being attached to the interior surface of at least one longitudinally extending side seal disposed between the proximal edge and the respective side edge of the chassis;".

Column 20
Line 17, after the word "attached" insert -- to the surface of --.

Line 18, delete "-its-" and insert -- the --.

Signed and Sealed this
Twenty-third Day of October, 2012

David J. Kappos
*Director of the United States Patent and Trademark Office*